(12) United States Patent
Wu et al.

(10) Patent No.: US 10,071,998 B2
(45) Date of Patent: Sep. 11, 2018

(54) IMINOTHIADIAZINE DIOXIDES BEARING AN AMINE-LINKED SUBSTITUENT AS BACE INHIBITORS, COMPOSITIONS, AND THEIR USE

(71) Applicant: Merck Sharp & Dohme Corp., Rahway, NJ (US)

(72) Inventors: Wen-Lian Wu, Green Brook, NJ (US); Shuwen He, Fanwood, NJ (US); Shawn P. Walsh, Bridgewater, NJ (US); Jared N. Cumming, Winchester, MA (US)

(73) Assignee: Merck Sharp & Dohme Corp.

( * ) Notice: Subject to any disclaimer, the term of this patent is extended or adjusted under 35 U.S.C. 154(b) by 0 days.

(21) Appl. No.: 15/543,608

(22) PCT Filed: Jan. 15, 2016

(86) PCT No.: PCT/US2016/013509
§ 371 (c)(1),
(2) Date: Jul. 14, 2017

(87) PCT Pub. No.: WO2016/118404
PCT Pub. Date: Jul. 28, 2016

(65) Prior Publication Data
US 2017/0369484 A1    Dec. 28, 2017

Related U.S. Application Data

(60) Provisional application No. 62/105,518, filed on Jan. 20, 2015.

(51) Int. Cl.
*C07D 417/14* (2006.01)
*C07D 417/12* (2006.01)

(52) U.S. Cl.
CPC .......... *C07D 417/14* (2013.01); *C07D 417/12* (2013.01)

(58) Field of Classification Search
CPC ........................... C07D 417/14; C07D 417/12
USPC ............................................................ 544/8
See application file for complete search history.

(56) References Cited

U.S. PATENT DOCUMENTS

| 7,763,609 | B2 | 7/2010 | Zhu et al. |
| 8,183,252 | B2 | 5/2012 | Zhu et al. |
| 8,557,826 | B2 | 10/2013 | Stamford et al. |
| 8,563,543 | B2 | 10/2013 | Scott et al. |
| 8,691,831 | B2 | 4/2014 | Zhu et al. |
| 8,691,833 | B2 | 4/2014 | Zhu et al. |
| 8,729,071 | B2 | 5/2014 | Scott et al. |
| 8,829,036 | B2 | 9/2014 | Zhu et al. |
| 8,940,748 | B2 | 1/2015 | Scott et al. |
| 9,029,362 | B2 | 5/2015 | Scott et al. |
| 9,428,475 | B2 | 8/2016 | Scott et al. |
| 9,475,785 | B2 | 10/2016 | Scott et al. |
| 9,499,502 | B2 | 11/2016 | Wu et al. |
| 2009/0082560 | A1 | 3/2009 | Kobayashi et al. |
| 2012/0183563 | A1 | 7/2012 | Scott et al. |
| 2014/0107027 | A1 | 4/2014 | Kong et al. |
| 2014/0275058 | A1 | 9/2014 | Minatti et al. |
| 2016/0367563 | A1 | 12/2016 | Scott et al. |

FOREIGN PATENT DOCUMENTS

WO    2015187437 A1    12/2015

OTHER PUBLICATIONS

International Search Report for PCT/US2014/13509 dated Mar. 28, 2016, 6 pages.

*Primary Examiner* — Kahsay Habte
(74) *Attorney, Agent, or Firm* — Keith D. MacMillan; Catherine D. Fitch

(57) ABSTRACT

In its many embodiments, the present invention provides certain iminothiazine dioxide compounds, including compounds Formula (I): or a tautomers thereof, and pharmaceutically acceptable salts of said compounds and said tautomers, wherein $R^1$, $R^2$, ring A, $R^A$, m, ring B, $R^B$, and n are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

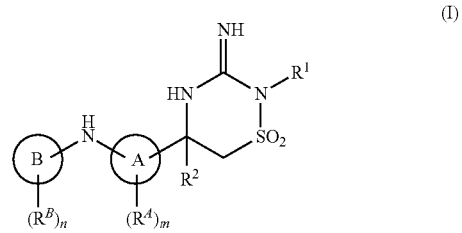

10 Claims, No Drawings

IMINOTHIADIAZINE DIOXIDES BEARING AN AMINE-LINKED SUBSTITUENT AS BACE INHIBITORS, COMPOSITIONS, AND THEIR USE

FIELD OF THE INVENTION

This invention provides certain iminothidiazine dioxide compounds bearing an amine-linked substituent, and compositions comprising these compounds, as inhibitors of BACE, which may be useful for treating or preventing pathologies related thereto.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), (β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE-1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types. Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, Loane, et al. report the targeting of amyloid precursor protein secretases as therapeutic targets for traumatic brain injury. (Loane et al., "Amyloid precursor protein secretases as therapeutic targets for traumatic brain injury", Nature Medicine, Advance Online Publication, published online Mar. 15, 2009; Yu, et al., "Lithium reduces BACE1 overexpression, β amyloid accumulation, and spatial learning deficits in mice with traumatic brain injury", J Neurotrauma, 2012 September; 29(13):2342-51; Tran, et al., "Controlled cortical impact traumatic brain injury in 3×Tg-AD mice causes acute intraaxonal amyloid-β accumulation and independently accelerates the development of tau abnormalities", J Neurosci. 2011 Jun. 29; 31(26):9513-25.) Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

SUMMARY OF THE INVENTION

The present invention provides certain iminothidiazine dioxide compounds bearing an amine-linked substituent, which are collectively or individually referred to herein as "compound(s) of the invention", as described herein. The compounds of the invention are inhibitors of BACE-1 and/or BACE-2, and may be useful for treating or preventing diseases or pathologies related thereto.

In one embodiment, the compounds of the invention have the structural Formula (I):

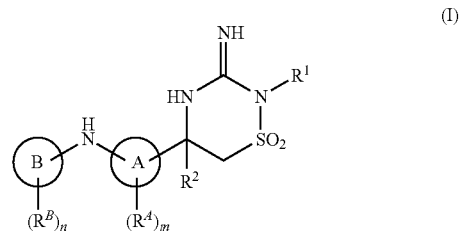

or a tautomer thereof having the structural Formula (I'):

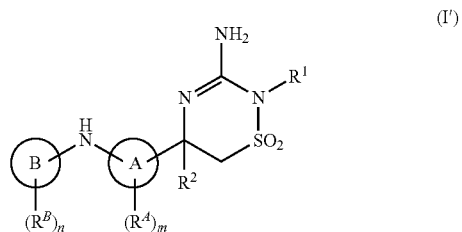

or pharmaceutically acceptable salt thereof, wherein:

$R^1$ is selected from the group consisting of H, lower alkyl, lower cycloalkyl, and -(lower alkyl)-(lower cycloalkyl),
  wherein said lower alkyl, lower cycloalkyl, and -(lower alkyl)-(lower cycloalkyl) are optionally substituted with one or more fluorine, and
  wherein 1 to 2 non-adjacent, non-terminal carbon atoms in said alkyl are optionally independently replaced with —O—, —NH—, —N-(lower alkyl)-, —S—, —S(O)—, or —S(O)$_2$—;

$R^2$ is selected from the group consisting of H, lower alkyl, lower cycloalkyl, and -(lower alkyl)-(lower cycloalkyl),
  wherein said lower alkyl, lower cycloalkyl, and -(lower alkyl)-(lower cycloalkyl) are optionally substituted with one or more fluorine, and
  wherein 1 to 2 non-adjacent, non-terminal carbon atoms in said alkyl are optionally independently replaced with —O—, —NH—, —N-(lower alkyl)-, —S—, —S(O)—, or —S(O)$_2$—;

ring A is selected from the group consisting of phenyl, pyridinyl, pyridazinyl, pyrimidinyl, and pyrazinyl;

m is 0, 1, 2, or 3;

each $R^A$ (when present) is independently selected from the group consisting of halogen, —CN, —OCH$_3$, —O-cyclopropyl, methyl, cyclopropyl, —CH$_2$OCH$_3$, —CF$_3$, —CHF$_2$, —CH$_2$F, —OCF$_3$, —OCHF$_2$, —OCH$_2$F, and —OCH$_2$CH$_2$F;

ring B is selected from the group consisting of benzimidazolyl, benzoisothiazolyl, benzoisoxazolyl, benzothiazolyl, benzoxazolyl, dihydrocyclopentapyridinyl, dihydroindenyl, imidazopyrazinyl, imidazopyridinyl, imidazopyrimidinyl, imidazothiazolyl, indenyl, indolyl, isoquinolinyl, naphthyridinyl, phthalazinyl, pteridinyl, pyrazinopyridazinyl, pyrazolopyridinyl, pyrazolopyrimidinyl, pyridopyrazinyl, pyridopyridazinyl, pyridopyrimidinyl, pyrrolopyridinyl, pyrrolopyrimidinyl, quinazolinyl, quinolinyl, quinoxalinyl, tetrahydroisoquinolinyl, tetrahydroquinolinyl, and thienylpyridinyl;

n is 0, 1, 2, or 3; and each $R^B$ (when present) is independently selected from the group consisting of halogen, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —CH$_2$F, —OCF$_3$, —OCHF$_2$, —OCH$_2$F, and —OCH$_2$CH$_2$F.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formulas (I), (I'), (IA), or (IA'). In each of the embodiments described herein, each variable is selected independently of the other unless otherwise noted.

In one embodiment, the compounds of the invention have the structural Formula (IA):

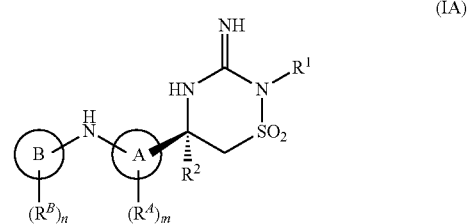

(IA)

or a tautomer thereof having the structural Formula (IA'):

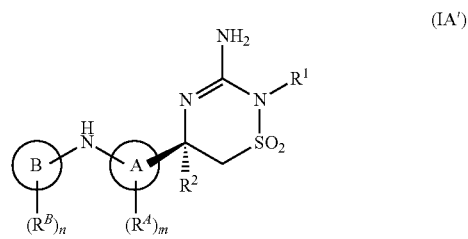

(IA')

or a pharmaceutically acceptable salt thereof, wherein each variable is as defined in Formula (I).

In one embodiment, in each of Formulas (I), (I'), (IA), and (IA'):

$R^1$ is selected from the group consisting of H, methyl, ethyl, cyclopropyl, —CH$_2$-cyclopropyl, and —CH$_2$CH$_2$OCH$_3$.

In one embodiment, in each of Formulas (I), (I'), (IA), and (IA'):

$R^1$ is selected from the group consisting of H and methyl.

In one embodiment, in each of Formulas (I), (I'), (IA), and (IA'):

$R^1$ is methyl.

In one embodiment, in each of Formulas (I), (I'), (IA), and (IA'):

$R^2$ is selected from the group consisting of H, methyl, ethyl, cyclopropyl, —CH$_2$-cyclopropyl, —CH$_2$F, —CHF$_2$, —CF$_3$, and —CH$_2$OCH$_3$.

In one embodiment, in each of Formulas (I), (I'), (IA), and (IA'):

$R^2$ is selected from the group consisting of methyl, cyclopropyl, and —CHF$_2$.

In one embodiment, in each of Formulas (I), (I'), (IA), and (IA'):

$R^2$ is methyl.

In one embodiment, in each of Formulas (I), (I'), (IA), and (IA'):

R¹ is selected from the group consisting of H, methyl, ethyl, cyclopropyl, —CH₂-cyclopropyl, and —CH₂CH₂OCH₃; and R² is selected from the group consisting of H, methyl, ethyl, cyclopropyl, —CH₂-cyclopropyl, —CH₂F, —CHF₂, —CF₃, and —CH₂OCH₃.

In one embodiment, in each of Formulas (I), (I'), (IA), and (IA'):

R¹ is selected from the group consisting of H and methyl; and

R² is selected from the group consisting of methyl, cyclopropyl, and —CHF₂.

In one embodiment, in each of Formulas (I), (I'), (IA), and (IA'):

R¹ is methyl; and
R² is methyl.

The following alternative embodiments of ring A, R^A, and m are applicable to each of the embodiments described hereinabove.

In one embodiment, in each of Formulas (I), (I'), (IA), and (IA'):

ring A is selected from the group consisting of phenyl, pyridinyl, and pyrimidinyl.

In one embodiment, in each of Formulas (I), (I'), (IA), and (IA'):

ring A is selected from the group consisting of phenyl and pyridinyl.

In one embodiment, in each of Formulas (I), (I'), (IA), and (IA'):

m is 0, 1 or 2; and
each R^A (when present) is independently selected from the group consisting of fluoro, chloro, —CN, —OCH₃, —CF₃, —CHF₂, —CH₂F, —OCF₃, —OCHF₂, and —OCH₂F.

In one embodiment, in each of Formulas (I), (I'), (IA), and (IA'):

m is 0, 1 or 2; and
each R^A (when present) is independently selected from the group consisting of fluoro, CN, —OCH₃, and —CHF₂.

In one embodiment, in each of Formulas (I), (I'), (IA), and (IA'):

m is 1 or 2; and
each R^A is fluoro.

In one embodiment, in each of Formulas (I), (I'), (IA), and (IA'):

ring A is selected from the group consisting of phenyl, pyridinyl, and pyrimidinyl;
m is 0, 1 or 2; and
each R^A (when present) is independently selected from the group consisting of fluoro, chloro, —CN, —OCH₃, —CF₃, —CHF₂, —CH₂F, —OCF₃, —OCHF₂, and —OCH₂F.

In one embodiment, in each of Formulas (I), (I'), (IA), and (IA'):

ring A is selected from the group consisting of phenyl and pyridinyl;
m is 0, 1 or 2; and
each R^A (when present) is independently selected from the group consisting of fluoro, chloro, —CN, —OCH₃, —CF₃, —CHF₂, —CH₂F, —OCF₃, —OCHF₂, and —OCH₂F.

In an alternative of the immediately preceeding embodiment, m is 0, 1 or 2; and
each R^A (when present) is independently selected from the group consisting of fluoro, CN, —OCH₃, and —CHF₂.

In another alternative of the immediately preceeding embodiment, m is 1 or 2; and
each R^A is fluoro.

In one embodiment, in each of Formulas (I), (I'), (IA), and (IA'):

ring A, R^A, and m form a moiety selected from the group consisting of

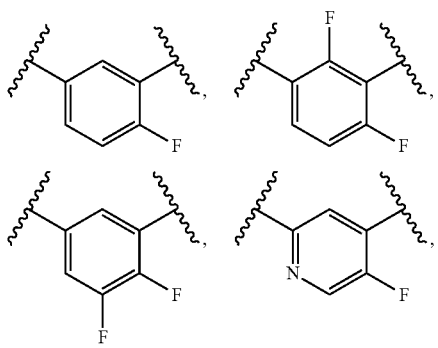

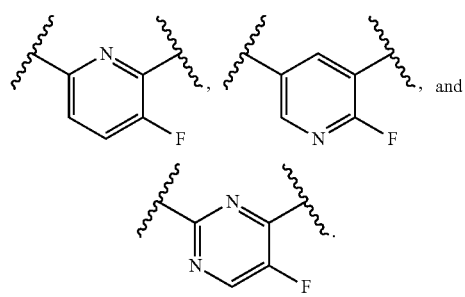

In one embodiment, in each of Formulas (I), (I'), (IA), and (IA'):

ring A, R^A, and m form a moiety selected from the group consisting of

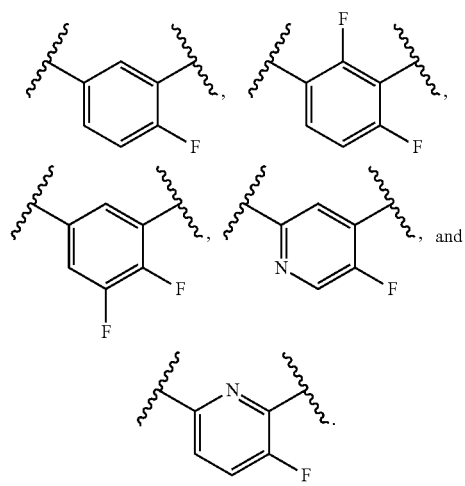

In one embodiment, in each of Formulas (I), (I'), (IA), and (IA'):

ring A, R^A, and m form a moiety selected from the group consisting of

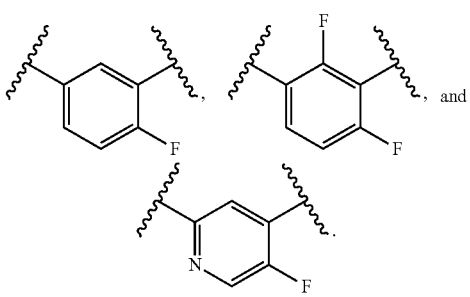

In one embodiment, in each of Formulas (I), (I'), (IA), and (IA'):

ring A, $R^A$, and m form a moiety selected from the group consisting of

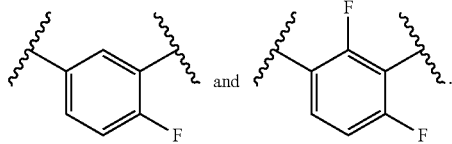 [SMILES: *c1ccc(F)c(*)c1 ; *c1ccc(F)c(*)c1F]

The following alternative embodiments of ring B, $R^B$ and n are contemplated in combination with each of the embodiments described hereinabove.

In one embodiment, in each of Formulas (I), (I'), (IA), and (IA'):

ring B is selected from the group consisting of dihydrocyclopentapyridinyl, dihydroindenyl, isoquinolinyl, naphthyridinyl, phthalazinyl, pteridinyl, pyrazinopyridazinyl, pyrazolopyridinyl, pyrazolopyrimidinyl, pyridopyrazinyl, pyridopyridazinyl, pyridopyrimidinyl, quinazolinyl, quinolinyl, quinoxalinyl, tetrahydroisoquinolinyl, and tetrahydroquinolinyl.

In one embodiment, in each of Formulas (I), (I'), (IA), and (IA'):

ring B is selected from the group consisting of dihydrocyclopentapyridinyl, dihydroindenyl, naphthyridinyl, pteridinyl, pyridopyrazinyl, pyridopyrimidinyl, and tetrahydroquinolinyl.

In one embodiment, in each of Formulas (I), (I'), (IA), and (IA'):

ring B is selected from the group consisting of 6,7-dihydro-5H-cyclopenta[b]pyridinyl, 2,3-dihydro-1H-indene, 1,5-naphthyridinyl, 1,7-naphthyridinyl, pteridinyl, pyrido[3,4-b]pyrazine, pyrido[3,2-d]pyrimidine, and 5,6,7,8-tetrahydroquinoline.

In another embodiment, in each of Formulas (I), (I'), (IA), and (IA'):

n is 0, 1, 2, or 3; and each $R^B$ (when present) is independently selected from the group consisting of fluoro, chloro, bromo, iodo, —CN, —OH, methyl, ethyl, cyclopropyl, —CH$_2$OCH$_3$, —C≡CH, —C≡C—CH$_3$, —CF$_3$, —CHF$_2$, —CH$_2$F, —OCH$_3$, —OCH$_2$—C≡C—H, —OCH$_2$—C≡C—CH$_3$, —OCF$_3$, —OCHF$_2$, and —OCH$_2$F.

In an alternative of the immediately preceeding embodiment, n is 0, 1, or 2. In another alternative of the immediately preceeding embodiment, n is 0 or 1. In another alternative of the immediately preceeding embodiment, n is 1.

In another embodiment, in each of Formulas (I), (I'), (IA), and (IA'):

n is 0, 1, 2, or 3; and each $R^B$ (when present) is independently selected from the group consisting of fluoro, chloro, bromo, —CN, —OH, —CH$_3$, —CHF$_2$, —CH$_2$F, —OCH$_3$, —OCH$_2$—C≡C—H, —OCH$_2$—C≡C—CH$_3$.

In an alternative of the immediately preceeding embodiment, n is 0, 1, or 2. In another alternative of the immediately preceeding embodiment, n is 0 or 1. In another alternative of the immediately preceeding embodiment, n is 1.

In another embodiment, in each of Formulas (I), (I'), (IA), and (IA'):

n is 0, 1, 2, or 3; and each $R^B$ (when present) is independently selected from the group consisting of bromo, —CN, —OCH$_3$, and —OCH$_2$—C≡C—CH$_3$.

In an alternative of the immediately preceeding embodiment, n is 0, 1, or 2. In another alternative of the immediately preceeding embodiment, n is 0 or 1. In another alternative of the immediately preceeding embodiment, n is 1.

In one embodiment, in each of Formulas (I), (I'), (IA), and (IA'):

ring B is selected from the group consisting of dihydrocyclopentapyridinyl, dihydroindenyl, isoquinolinyl, naphthyridinyl, phthalazinyl, pteridinyl, pyrazinopyridazinyl, pyrazolopyridinyl, pyrazolopyrimidinyl, pyridopyrazinyl, pyridopyridazinyl, pyridopyrimidinyl, quinazolinyl, quinolinyl, quinoxalinyl, tetrahydroisoquinolinyl, and tetrahydroquinolinyl;

n is 0, 1, 2, or 3; and each $R^B$ (when present) is independently selected from the group consisting of fluoro, chloro, bromo, iodo, —CN, —OH, methyl, ethyl, cyclopropyl, —CH$_2$OCH$_3$, —C≡CH, —C≡C—CH$_3$, —CF$_3$, —CHF$_2$, —CH$_2$F, —OCH$_3$, —OCH$_2$—C≡C—H, —OCH$_2$—C≡C—CH$_3$, —OCF$_3$, —OCHF$_2$, and —OCH$_2$F.

In an alternative of the immediately preceeding embodiment, n is 0, 1, or 2. In another alternative of the immediately preceeding embodiment, n is 0 or 1. In another alternative of the immediately preceeding embodiment, n is 1.

In one embodiment, in each of Formulas (I), (I'), (IA), and (IA'):

ring B is selected from the group consisting of dihydrocyclopentapyridinyl, dihydroindenyl, naphthyridinyl, pteridinyl, pyridopyrazinyl, pyridopyrimidinyl, and tetrahydroquinolinyl;

n is 0, 1, 2, or 3; and each $R^B$ (when present) is independently selected from the group consisting of fluoro, chloro, bromo, —CN, —OH, —CH$_3$, —CHF$_2$, —CH$_2$F, —OCH$_3$, —OCH$_2$—C≡C—H, —OCH$_2$—C≡C—CH$_3$.

In an alternative of the immediately preceeding embodiment, n is 0, 1, or 2. In another alternative of the immediately preceeding embodiment, n is 0 or 1. In another alternative of the immediately preceeding embodiment, n is 1.

In one embodiment, in each of Formulas (I), (I'), (IA), and (IA'):

ring B is selected from the group consisting of 6,7-dihydro-5H-cyclopenta[b]pyridinyl, 2,3-dihydro-1H-indene, 1,5-naphthyridinyl, 1,7-naphthyridinyl, pteridinyl, pyrido[3,4-b]pyrazine, pyrido[3,2-d]pyrimidine, and 5,6,7,8-tetrahydroquinoline;

n is 0, 1, 2, or 3; and each $R^B$ (when present) is independently selected from the group consisting of bromo, —CN, —OCH$_3$, and —OCH$_2$—C≡C—CH$_3$.

In an alternative of the immediately preceeding embodiment, n is 0, 1, or 2. In another alternative of the immediately preceeding embodiment, n is 0 or 1. In another alternative of the immediately preceeding embodiment, n is 1.

In another embodiment, in each of Formulas (I), (I'):

ring B, $R^B$, and n form a moiety selected from the group consisting of:

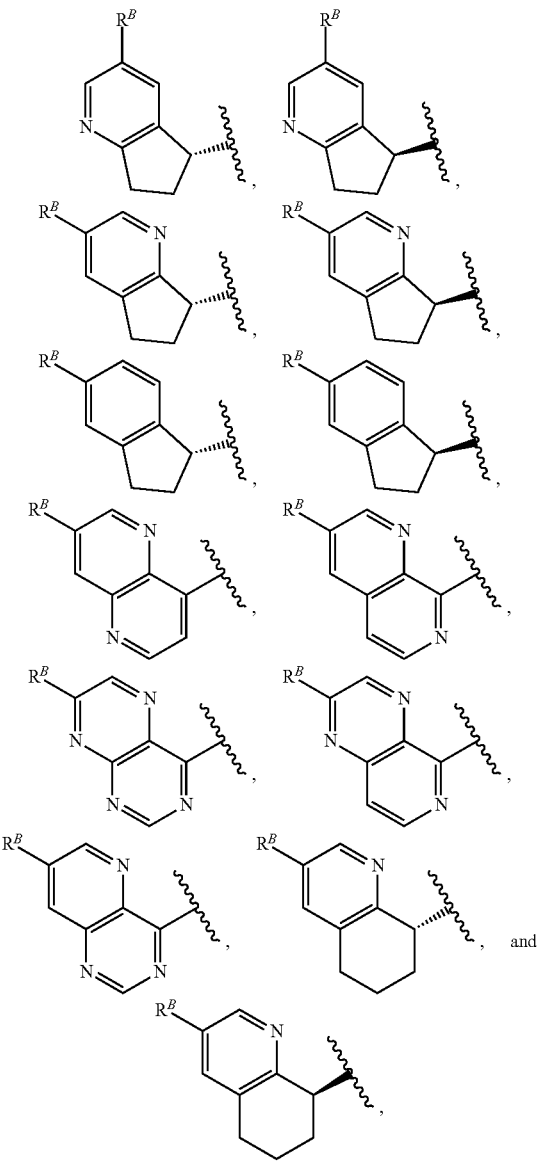

wherein $R^B$ is selected from the group consisting of fluoro, chloro, bromo, —CN, —OCH$_3$, —CHF$_2$, and —CF$_3$.

In another embodiment, in each of Formulas (I), (I'):

ring B, $R^B$, and n form a moiety selected from the group consisting of:

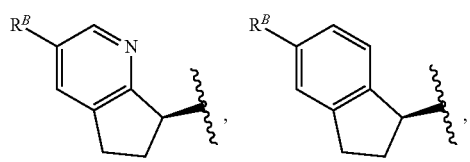

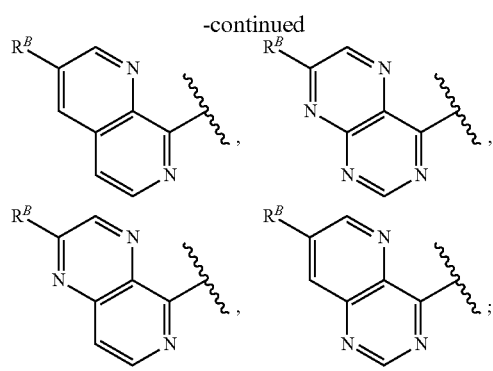

wherein $R^B$ is selected from the group consisting of fluoro, chloro, bromo, —CN, —OCH$_3$, —CHF$_2$, and —CF$_3$.

In another embodiment, in each of Formulas (I), (I'):

ring B, $R^B$, and n form a moiety selected from the group consisting of:

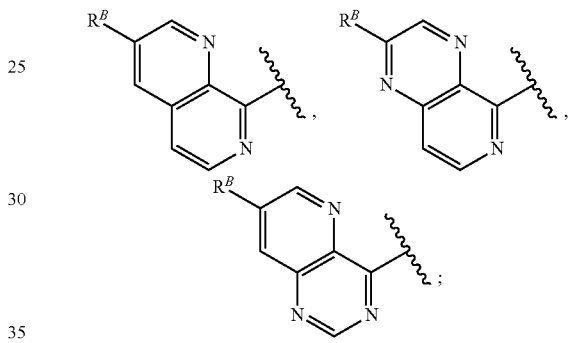

wherein $R^B$ is selected from the group consisting of fluoro, —CN, —OCH$_3$, and —CHF$_2$.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In another embodiment, 1 to 3 carbon atoms of the compounds of the invention may be replaced with 1 to 3 silicon atoms so long as all valency requirements are satisfied.

In another embodiment, there is provided a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1 H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" protion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine, chlorine, bromine, or iodine. Preferred are fluorine, chlorine and bromine.

"Alkyl" means an aliphatic hydrocarbon group, which may be straight or branched, comprising 1 to about 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halo group defined above.

"Cycloalkyl" means a non-aromatic monocyclic or multicyclic ring system comprising about 3 to about 10 carbon atoms, preferably about 3 to about 6 carbon atoms. Monocyclic cycloalkyl refers to monocyclic versions of the cycloalkyl moieties described herein. "Lower cycloalkyl" means —($C_3$-$C_6$)cycloalkyl. Non-limiting examples of suitable monocyclic cycloalkyls include cyclopropyl, cyclobutyl, cyclopentyl, cyclohexyl, cycloheptyl and the like. Non-limiting examples of multicyclic cycloalkyls include [1,1,1]-bicyclopentane, 1-decalinyl, norbornyl, adamantyl and the like.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl moiety or the like includes substitution on any ring portion and/or on the alkyl portion of the group.

When a variable appears more than once in a group, e.g., $R^6$ in —$N(R^6)_2$, or a variable appears more than once in a structure presented herein, the variables can be the same or different.

The line —, as a bond generally indicates a mixture of, or either of, the possible isomers, e.g., containing (R)— and (S)— stereochemistry. For example:

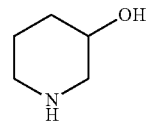

means containing both

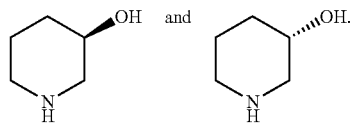

The wavy line, ~~~ as used herein, indicates a point of attachment to the rest of the compound. Lines drawn into the ring systems, such as, for example:

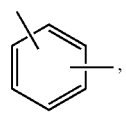

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

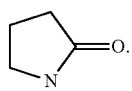

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

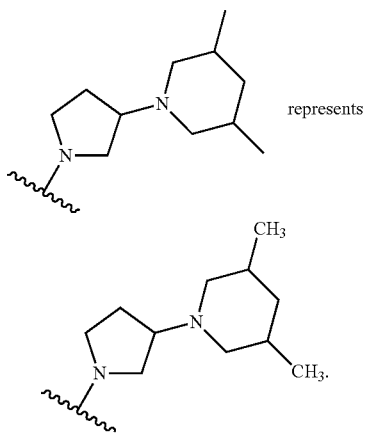 represents

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, a compounds of the invention conforming to the formula:

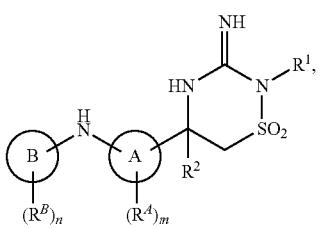

and its tautomer, which can be depicted as:

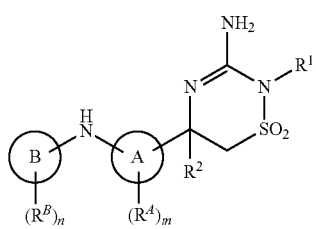

are both contemplated as being within the scope of the compounds of the invention. As noted above, while only one said tautomeric form of each compound is shown in the tables and appended claims, it shall be understood that both tautomeric forms of the compounds are contemplated as being within the scope of the non-limiting example compounds of the invention. Thus, as should be clear from the foregoing, the compounds of examples in the table below may alternatively be depicted, and exist, as their respective tautomers.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). For example, if a compound of the invention incorporates a double bond or a fused ring, both the cis- and trans-forms, as well as mixtures, are embraced within the scope of the invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation compring one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

PREPARATIVE EXAMPLES

Compounds of the invention can be made using procedures known in the art. The following reaction schemes show typical procedures, but those skilled in the art will recognize that other procedures can also be suitable. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follows:

Acetonitrile: MeCN, ACN
Aqueous: aq.
tert-Butanol: t-BuOH
BrettPhos G3 precatalyst: [(2-Di-cyclohexylphosphino-3,6-dimethoxy-2',4',6'-triisopropyl-1,1'-biphenyl)-2-(2'-amino-1,1'-biphenyl)]palladium(II) methanesulfonate
BrettPhos Palladacycle: chloro [2-(dicyclohexylphosphino)-3,6-dimethoxy-2',4',6'-tri-i-propyl-1,1'-biphenyl][2-(2-aminoethyl)phenyl]palladium(II)
Concentrated: conc.
tris-(Dibenzylideneacetone)dipalladium: $Pd_2(dba)_3$
Di-tert-butyldicarbonate: $Boc_2O$
Dichloromethane: DCM
Diethylaminosulfur trifluoride: DAST
Diisopropylethylamine: DIEA or $iPr_2NEt$
Dimethoxyethane: DME
N,N-Dimethylaminopyridine: DMAP
Dimethylacetamide: DMA
Dimethylformamide: DMF
Dimethylsulfoxide: DMSO
4,5-bis(Diphenylphosphino)-9,9-dimethylxanthene: Xantphos
Electrospray: ES
Ethanol: EtOH
Ethyl: Et
Ethyl acetate: AcOEt, EtOAc, or EA
Example: Ex.
Grams: g
Hexanes: hex
High performance liquid chromatography: HPLC
Hours: h
Isopropyl alcohol: IPA
Liquid chromatography mass Spectrometry: LCMS
Liter: L
Lithium bis(trimethylsilyl)amide: LHMDS or LiHMDS
Lithium diisopropylamide: LDA
Methanol: MeOH
Methylmagnesium bromide: MeMgBr
Microliters: μl or μL or uL
Milligrams: mg
Milliliters: mL
Millimoles: mmol
Micromoles: uM or μM
Minutes: min
Molar: M
n-Butyllithium: nBuLi or n-BuLi
Normal: N
Nuclear magnetic resonance spectroscopy: NMR
Palladium on carbon: Pd/C
Palladium acetate: $Pd(OAc)_2$
Petroleum ether: PE
Preparative: prep-, p-
Room temperature (ambient, about 25° C.): rt or RT
RuPhos G2 precatalyst: Chloro(2-dicyclohexylphosphino-2',6'-diisopropoxy-1,1'-biphenyl)[2-(2'-amino-1,1'-biphenyl)]palladium(II), RuPhos-Pd-G2
Saturated: sat.
Silica gel: $SiO_2$
Supercritical Fluid Chromatography: SFC
tert-Butoxycarbonyl: t-Boc or Boc
Temperature: temp.
Tetrahydrofuran: THF
Thin layer chromatography: TLC
Titanium(IV)ethoxide: $Ti(OEt)_4$
Triethylamine: $Et_3N$ or TEA
Trifluoroacetic acid: TFA
Trimethylsilyl: TMS-bis(Triphenylphosphine)palladium (II)dichloride: $Pd(PPh_3)_2Cl_2$ Method A

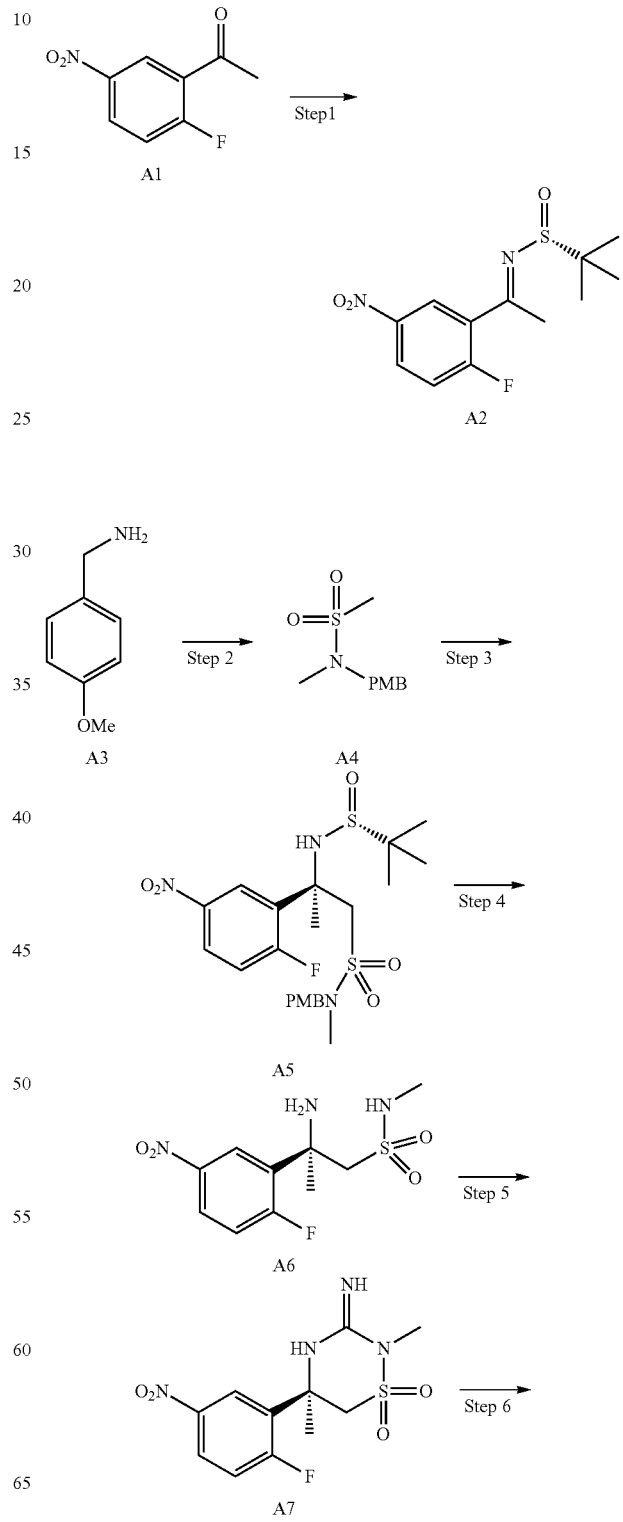

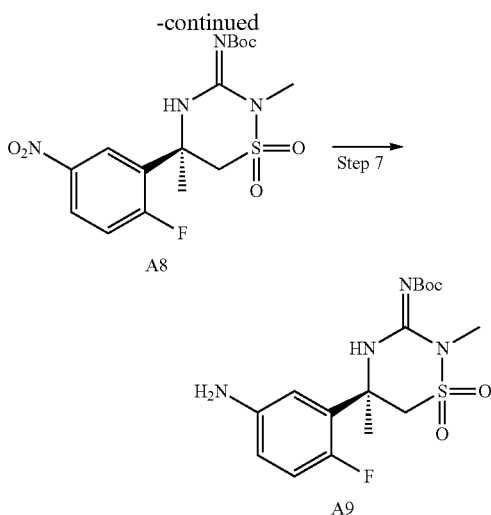

Step 1

To a solution of acetophenone A1 (115 g, 628 mmol) in anhydrous THF (900 mL) was added (R)-t-butylsulfinimde (83.7 g, 691 mmol) and Ti(OEt)$_4$ (315 g, 1.38 mol). The resultant solution was heated to reflux for 20 hr. The solution was then cooled to RT and poured onto ice (3 kg). The resultant mixture was stirred for 20 min. The mixture was then filtered and the filter cake was washed with CH$_2$Cl$_2$ (3×). The layers were separated and the organic layer was washed with brine, dried over Na$_2$SO$_4$, filtered and concentrated. The crude product was purified via flash chromatography (SiO$_2$; 15% EtOAc/heptane) to afford the ketimine A2.

Step 2

To a stirred solution of 4-methoxybenzyl amine A3 (199 g, 1.45 mol) in anhydrous pyridine (400 mL) at 0° C. was added dropwise via an addition funnel methanesulfonyl chloride (116 mL, 1.45 mol) over 45 min. After the addition was complete, the cooling bath was removed and the resultant solution was stirred at RT overnight. The reaction was concentrated in vacuo. The slurry was then taken up in DCM (1 L). The organic solution was washed with 1 N HCl (aq.) (2×1 L), sat. NaHCO$_3$ (2×1 L) and brine (1×500 mL). The organic layer was dried over Na$_2$SO$_4$, filtered and concentrated to afford a solid. This solid was dissolved in 95% EtOH (430 mL) with warming. The solution was allowed to cool, and the resulting solid precipitate was removed by filtration. The solid was then washed with cold EtOH (3×150 mL). A second crop of solid was similarly obtained after allowing the mother liquor to stir at RT overnight. The combined solids were dissolved in anhydrous DMF (3.0 L), cooled to 0° C. and placed under an atmosphere of N$_2$. To this solution was added in small portions sodium hydride (60% in mineral oil, 60.2 g, 1.51 mol). After the addition was complete, the mixture was stirred for an additional 10 min. To this mixture was added dropwise via an addition funnel methyl iodide (250 g, 1.76 mol). After the addition was complete, the cooling bath was removed and the mixture was allowed to stir at RT overnight. After that time, the mixture was concentrated in vacuo to remove approximately 2.5 L of DMF. The mixture was then partitioned between 5 L ice water and 5 L Et$_2$O with 500 mL of EtOAc. The organic layer was separated. The aqueous layer was extracted with Et$_2$O (2×1 L). The combined organic layers were washed with brine (2×1 L), dried over Na$_2$SO$_4$, filtered and concentrated. The residue was stirred with hexanes, and the resulting solid was removed by filtration and washed with hexanes (2×250 mL). This solid was then dissolved in hexanes/EtOAc (1:1, 450 mL) with warming. The solid formed on cooling was filtered off to afford product A4. The remaining mother liquor was purified via silica gel chromatography (50% EtOAc/hexanes) to afford additional A4.

Step 3

To a solution of sulfonamide A4 (38.0 g, 166 mmol) in anhydrous THF (500 mL) at −78° C. under an atmosphere of N$_2$ was slowly added a solution of n-BuLi (1.6 M in hexanes, 104 mL, 166 mmol). The resultant solution was stirred at −78° C. for 30 min. After that time, a precooled (−78° C.) solution of ketimine A2 (23.7 g, 82.8 mmol) in anhydrous THF (200 mL) was added to the reaction mixture via cannula. The resulting mixture was allowed to stir at −78° C. for 1 hour. After that time, water and EtOAc were added to the reaction. The cooling bath was removed and the mixture was allowed to warm to RT. The aqueous layer was then separated and extracted with EtOAc (3×). The combined organic layers were washed with brine, dried over Na$_2$SO$_4$, filtered and concentrated. The crude product was purified via flash chromatography (SiO$_2$; gradient elution 100:0 to 40:60 hexanes:EtOAc) to afford A5.

Step 4

To a solution of A5 (27.4 g, 53.1 mmol) in CH$_2$Cl$_2$: MeOH (3:1, 230 mL) was added a solution of HCl (4 M in dioxane, 80 mL, 319 mmol). The resultant solution was stirred at RT for 45 min. The solution was then concentrated. The crude residue was taken up in toluene (100 mL) and concentrated in vacuo (2×). The residue was dissolved in CH$_2$Cl$_2$ (230 mL). To this solution were added TFA (61.4 mL, 797 mmol) and 1,3-dimethoxybenzene (42 mL, 319 mmol). The resultant solution was stirred at RT overnight. The solution was then concentrated to approximately ¼ the original volume. The solution was partitioned between 1 M HCl (aq.) (1 L) and Et$_2$O (500 mL). The aqueous layer was separated and extracted with Et$_2$O (2×500 mL). The organic layers were combined and back-extracted with 1 N HCl (1×250 mL). The aqueous layers were then combined, adjusted to approximately pH 10 with the slow addition of solid Na$_2$CO$_3$, and then extracted with CH$_2$Cl$_2$ (4×300 mL). The organic layers were combined, dried over Na$_2$SO$_4$, filtered and concentrated to afford A6.

Step 5

To a slurry of amine A6 (13.7 grams, 47 mmol) in n-butanol (150 mL) was added a solution of cyanogen bromide (5M in MeCN, 10.3 mL, 51 mmol). The resultant mixture was heated to reflux for 4 hours. The mixture was then concentrated to approximately ⅓ of the original volume. To the mixture was added Et$_2$O (200 mL). The resultant solid was removed via filtration and the solid was washed with Et$_2$O (2×). The solid was partitioned between EtOAc and sat. Na$_2$CO$_3$ (aq.). The aqueous layer was extracted with EtOAc (3×). The combined organic layers were washed with brine, dried over Na$_2$SO$_4$, filtered and concentrated to afford A7. This material was carried onto the next step without further purification.

Step 6

To a solution of A7 (4.0 grams 11.6 mmol) in CH$_2$Cl$_2$ (100 mL) was added Et$_3$N (2.26 mL, 16.2 mmol) and Boc$_2$O (3.3 g, 15.1 mmol). The resultant solution was stirred at RT overnight. After that time, the solution was washed with sat. Na$_2$CO$_3$ (aq.). The aqueous layer was back-extracted with CH$_2$Cl$_2$ (3×). The combined organic layers were dried over Na$_2$SO$_4$, filtered and concentrated. The crude product was purified via flash chromatography (SiO$_2$, gradient elution 100:0 to 70:30 hexanes:EtOAc) to afford A8.

Step 7

A solution of A8 (2.50 g, 6.0 mmol) in EtOH (150 mL) was purged with bubbling $N_2$ for 3 min. To this solution was added Pd/C (10% w/w, 50% $H_2O$, 698 mg). The atmosphere was evacuated and back-filled with $H_2$ (3×). The resulting mixture was stirred at RT under a $H_2$ balloon for 2 hrs. After that time, the mixture was purged with $N_2$. The mixture was then filtered through Celite and concentrated. The residue was filtered through a small pad of silica gel eluting with EtOAc to afford A9. This material was used without further purification.

The following intermediate was prepared in a similar manner that that described in Method A using the requisite acetophenone instead of A1 in step 1.

tion and solid sodium hydroxide. The resulting mixture was extracted with ethyl acetate, and the combined organic layers were dried over magnesium sulfate and concentrated. This crude residue was dissolved in 20 mL of DCM, and $(Boc)_2O$ (1.29 g, 5.9 mmol), and DIEA (2.56 mL, 14.75 mmol) were added. The reaction was stirred overnight, and then quenched with 1N HCl. The mixture was extracted with DCM, the organic portions were combined, dried over magnesium sulfate, and concentrated. The crude residue was purified by a flash silica column (25% ethyl acetate/hexane) to give product A1-1.

Step 2:

Compound A1-1 was treated in an analogous manner to that described in Method A, step 7 to afford compound A1-2.

Method B

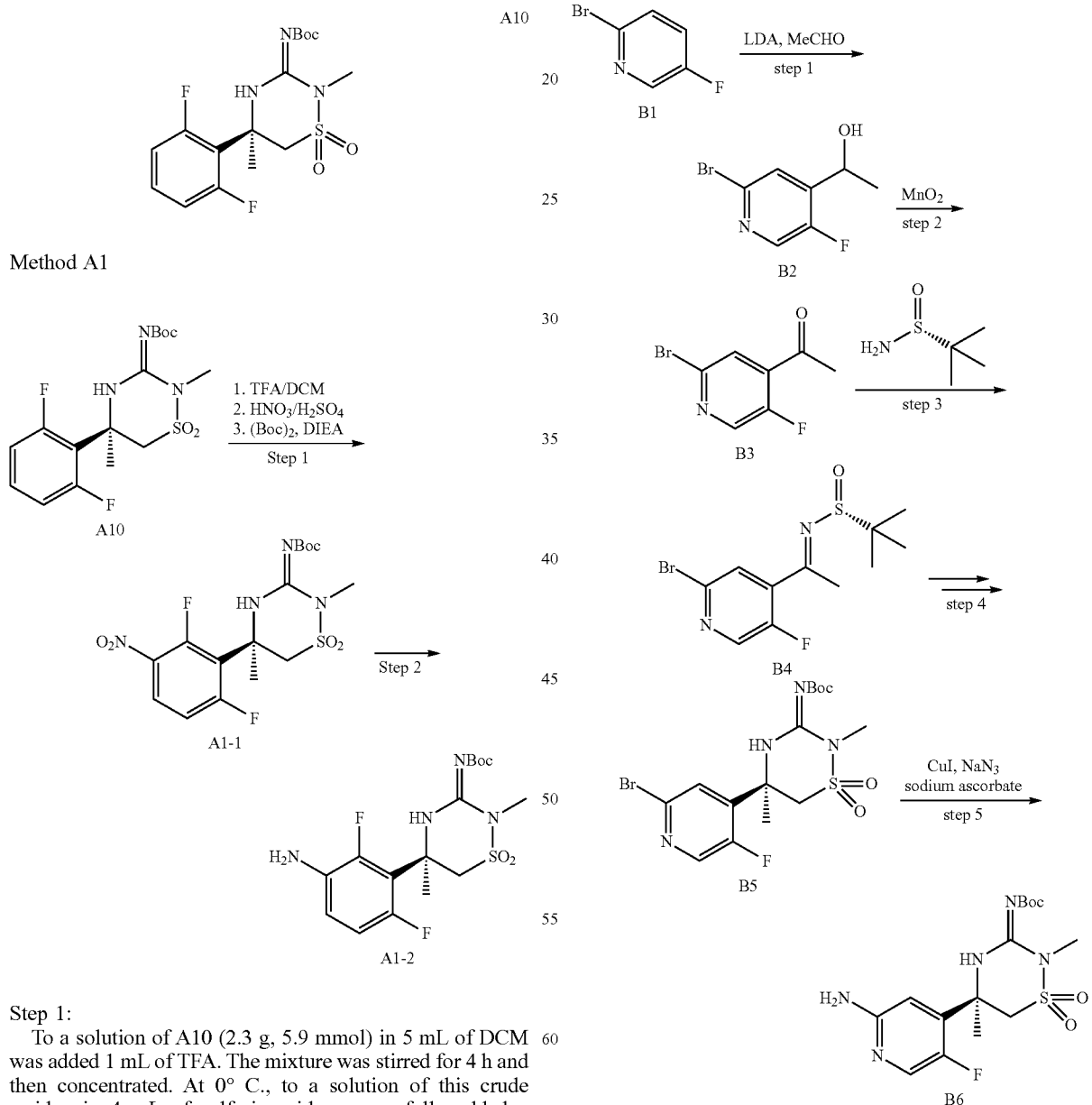

Method A1

Step 1:

To a solution of A10 (2.3 g, 5.9 mmol) in 5 mL of DCM was added 1 mL of TFA. The mixture was stirred for 4 h and then concentrated. At 0° C., to a solution of this crude residue in 4 mL of sulfuric acid was carefully added a mixture of 0.5 mL of fuming nitric acid and 1.2 mL of sulfuric acid. The mixture was stirred at 0° C. for 2 h and then poured into 150 mL of ice. The mixture was neutralized by addition of saturated aqueous sodium bicarbonate solu-

Step 1

To a solution of 2-bromo-5-fluoropyridine B1 (50.0 g, 0.290 mol) in THF (300 mL) was added LDA (150 mL, 0.290 mol, 2 M in THF) at −78° C. After stirring at −78° C. for 2 h, acetaldehyde (13.8 g, 0.34 mol) was added and the reaction mixture was allowed to warm to room temperature and stirred overnight. The reaction was quenched with saturated aqueous NH$_4$Cl and extracted with EtOAc. The combined organic extracts were washed with brine, dried over Na$_2$SO$_4$, filtered and concentrated. The residue was purified by column chromatography on silica gel (PE:EtOAc=10:1) to afford compound B2. MS for B2: m/e=220 and 222 (M+1).

Step 2

A suspension of 1-(2-bromo-5-fluoropyridin-4-yl) ethanol B2 (43.0 g, 0.20 mol) and MnO$_2$ (68.0 g, 0.80 mmol) in CHCl$_3$ (400 mL) was heated at reflux under N$_2$ atmosphere overnight. The reaction mixture was filtered and the filtrate was concentrated. The residue was purified by column chromatography (PE:EtOAc=20:1) to afford compound B3. MS for B3: m/e=218 and 220 (M+1).

Step 3

A mixture of 1-(2-bromo-5-fluoropyridin-4-yl) ethanone B3 (30.0 g, 0.140 mol), (R)-2-methyl-2-propanesulfinamide (25.0 g, 0.210 mol) and Ti(OEt)$_4$ (63.0 g, 0.280 mol) in THF (300 mL) was heated at reflux overnight. The mixture was quenched by ice-water (150 mL) and filtered. The filtrate was extracted with EtOAc. The combined extracts were washed with water and brine, dried over Na$_2$SO$_4$ and filtered. The filtrate was concentrated; the residue was purified by column chromatography (PE:EtOAc=10:1) to afford compound B4. MS for B4: m/e=321 and 323 (M+1).

Step 4

Compound B4 was transformed into compound B5 in a method similar to that described for A2 in Method A, steps 3 to 7.

Step 5

To a mixture of (R)-tert-butyl (5-(2-bromo-5-fluoropyridin-4-yl)-2,5-dimethyl-1,1-dioxido-1,2,4-thiadiazinan-3-ylidene)carbamate B5 (5.0 g, 11.08 mmol), sodium azide (4.32 g, 66.5 mmol), sodium ascorbate (1.097 g, 5.54 mmol) and copper(I) iodide(1.055 g, 5.54 mmol) in EtOH (50 ml) and H$_2$O (20 ml) was bubbled with nitrogen gas for 10 min. Trans-N,N'-dimethylcyclohexane-1,2-diamine (1.747 ml, 11.08 mmol) was added. The reaction mixture was heated at 50° C. under nitrogen for 2.5 hr. After addition of ammonium hydroxide (100 ml), the mixture was stirred for 10 min, and then extracted with EtOAc (3×100 ml). The organic layers were washed with brine, dried over MgSO$_4$ and concentrated. The residue was purified by chromatography (120 g of SiO$_2$, 0-60% EtOAc/hexane) to afford compound B6 (4.02 g). MS for B6: m/e=388 (M+1).

Method C

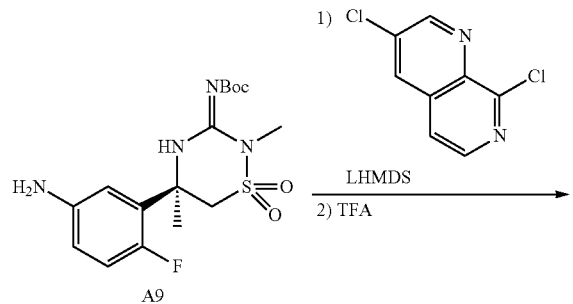

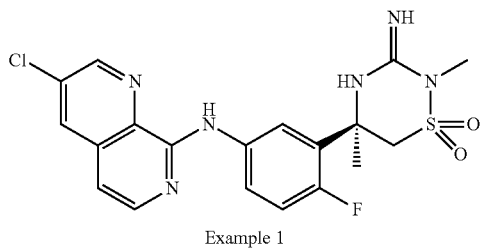

Example 1

Step 1

To a stirred solution of (R)-tert-butyl (5-(5-amino-2-fluorophenyl)-2,5-dimethyl-1,1-dioxido-1,2,4-thiadiazinan-3-ylidene)carbamate A9 (100 mg, 0.259 mmol) and 3,8-dichloro-1,7-naphthyridine (77 mg, 0.388 mmol) in THF (5.2 ml) was added LiHMDS in THF (1M in THF, 0.647 ml, 0.647 mmol) at RT. The mixture was stirred at 45° C. for 15 h. It was diluted with saturated aqueous ammonium chloride and extracted with DCM (3×). The combined organic layers were dried with magnesium sulfate, filtered and concentrated under reduced pressure. The solution was diluted with 5 mL of DCM and TFA (0.100 ml, 1.294 mmol) was added. The mixture was stirred at room temperature for 15 h. It was quenched with saturated aqueous sodium bicarbonate and extracted with DCM (3×). The combined organic layers were dried over magnesium sulfate, filtered and concentrated. The residue was purified by reverse phase HPLC (19×50 mm, Waters XBridge C18 column, 5μ particle size, ACN/H2O buffering with 0.16% ammonium) to afford example 1. MS for example 1: m/e=449 (M+1).

Examples 3-5 in Table 1 were prepared using conditions similar to those described in Method C from either A9 or B6, as appropriate, and using the requisite heteroaromatic coupling partner if other than 3,8-dichloro-1,7-naphthyridine.

Method D

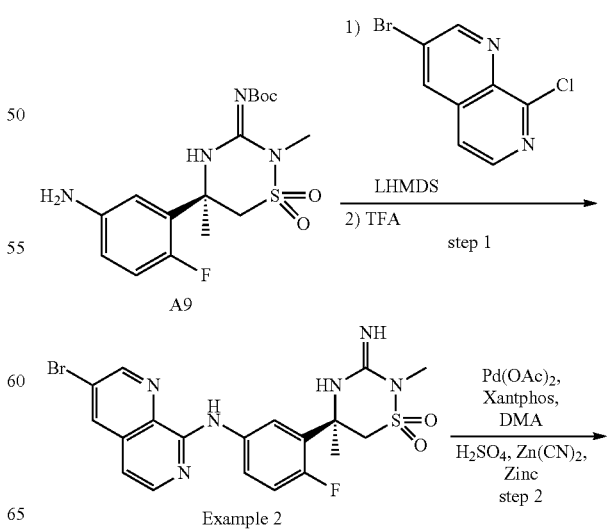

Example 2

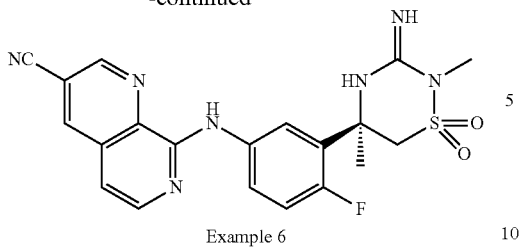

Example 6

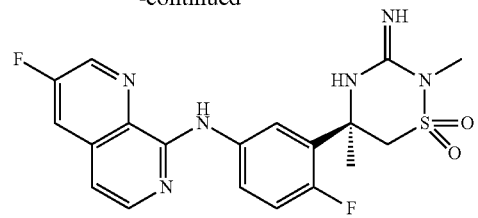

Example 8

Step 1

To a stirred solution of (R)-tert-butyl (5-(5-amino-2-fluorophenyl)-2,5-dimethyl-1,1-dioxido-1,2,4-thiadiazinan-3-ylidene)carbamate A9 (250 mg, 0.647 mmol) and 3-bromo-8-chloro-1,7-naphthyridine (205 mg, 0.841 mmol) in THF (6.47 ml) was added LiHMDS (1M in THF, 1.617 ml, 1.617 mmol) at room temperature. The mixture was stirred at 45° C. for 4 h. It was diluted with saturated ammonium chloride and extracted with DCM (3×). The organics were combined, dried over magnesium sulfate, filtered and concentrated. The residue was redissolved in DCM (3 mL) and TFA (0.249 ml, 3.23 mmol) added and the reaction stirred for 15 h. The reaction was quenched with saturated sodium bicarbonate and extracted with DCM (3×). The organic layers were combined, dried over magnesium sulfate, filtered and concentrated. The residue was purified by column chromatography EtOAc in DCM to afford example 2. MS for example 2: m/e=493 (M+1).

Step 2

To a solution of palladium acetate (4.55 mg, 0.020 mmol) and Xantphos (12 mg, 0.020 mmol) in DMA (2 mL) was added $H_2SO_4$ (1.1 µl, 0.020 mmol). The reaction was sealed, purged with $N_2$ for 5 min and then allowed to heat at 80° C. for 30 min after which the mixture was cooled to RT. Example 2 (100 mg, 0.203 mmol), $Zn(CN)_2$ (13 mg, 0.111 mmol), zinc (1.33 mg, 0.020 mmol) and DMA (2 mL) were added to a separate vial and purged with $N_2$ for 5 min. To this vial was introduced the catalyst solution via syringe. After the mixture was heated at 80° C. for 15 h, the mixture was quenched with saturated sodium bicarbonate and extracted with DCM. The combined organic layers were dried over magnesium sulfate, concentrated and purified by silica gel chromatography (EtOAc/DCM) to afford example 6. MS for example 6: m/e=440 (M+1).

Examples 7 and 11 was prepared using conditions similar to those described in Method D from either A9 or A1-2, as appropriate, and using the requisite heteroaromatic coupling partner in step 1 if other than 3-bromo-8-chloro-1,7-naphthyridine.

Method E

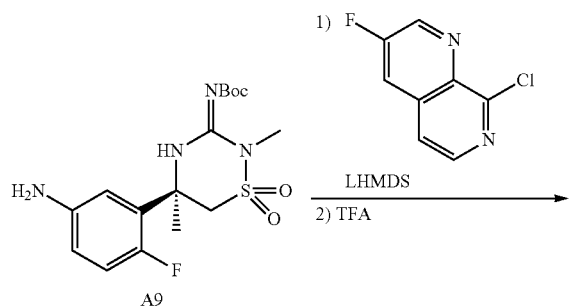

To a microwave reaction vial were added (R)-tert-butyl (5-(5-amino-2-fluorophenyl)-2,5-dimethyl-1,1-dioxido-1,2,4-thiadiazinan-3-ylidene)carbamate A9 (130 mg, 0.336 mmol), 8-chloro-3-fluoro-1,7-naphthyridine (67.6 mg, 0.37 mmol), LiHMDS (1.0 M in THF, 1.11 ml, 1.11 mmol) and THF (3.5 ml). The vial was capped and the reaction mixture was heated at 45° C. overnight. It was diluted with 10 ml of water and then extracted with DCM (20 ml×2). The combined organic extracts were washed with brine, dried over $MgSO_4$, and concentrated in vacuo. The residue was dissolved in 3 ml DCM and treated with TFA (1.0 ml, 12.98 mmol). It was stirred at rt under nitrogen for 1 hr and then concentrated in vacuo. The residue was purified by preparative TLC eluting with 5% 7N $NH_3$ in MEOH/DCM to afford example 8 (79 mg).

Method F

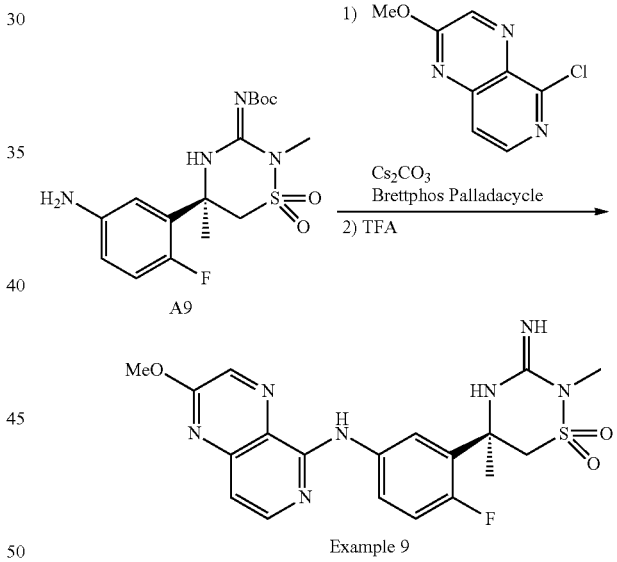

Example 9

To a microwave reaction vial were added (R)-tert-butyl (5-(5-amino-2-fluorophenyl)-2,5-dimethyl-1,1-dioxido-1,2,4-thiadiazinan-3-ylidene)carbamate A9 (100 mg, 0.259 mmol), 5-bromo-2-methoxypyrido[3,4-b]pyrazine (68.3 mg, 0.285 mmol), Brettphos palladacycle (10.34 mg, 0.013 mmol), $Cs_2CO_3$ (253 mg, 0.776 mmol) and dioxane (2.5 ml). Nitrogen was purged through the reaction mixture for 5 min and then the vial was capped. The reaction mixture was heated at 80° C. overnight. It was concentrated; the residue was partitioned between DCM and water. The organic layer was washed with brine, dried over $MgSO_4$ and concentrated in vacuo. The residue was dissolved in 3 ml DCM and treated with TFA (1.0 ml, 12.98 mmol). The reaction mixture was stirred at rt under nitrogen for 2.5 hr and then concentrated. The residue was purified by preparative TLC to afford example 9 (2.7 mg).

Method G

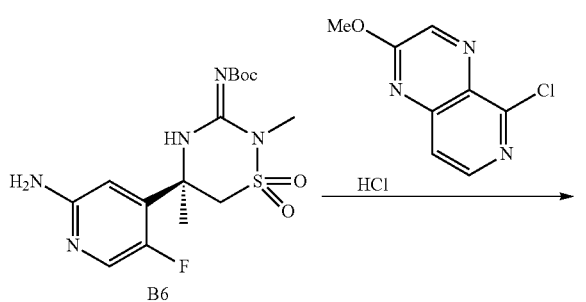

B6

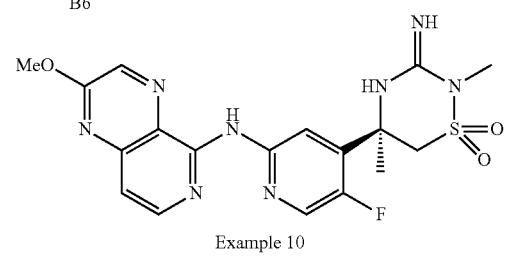

Example 10

To a solution of (R)-tert-butyl (5-(2-amino-5-fluoropyridin-4-yl)-2,5-dimethyl-1,1-dioxido-1,2,4-thiadiazinan-3-ylidene)carbamate B6 (120 mg, 0.310 mmol) in t-BuOH (5.0 ml) were added 5-chloro-2-methoxypyrido[3,4-b]pyrazine (60.6 mg, 0.310 mmol) and HCl (4.0 M in 1,4-dioxane, 155 μl, 0.619 mmol). This reaction mixture was heated at 100° C. overnight. It was concentrated; the residue was dissolved in water and basified with saturated NaHCO$_3$ to pH 9. It was extracted with DCM twice. The organic layers were washed with water, dried over MgSO$_4$ and concentrated. The residue was purified by chromatography (40 g of SiO$_2$, 0-5% 7N NH$_3$ in MeOH/DCM) followed by preparative TLC to afford example 10 (9 mg).

Method H

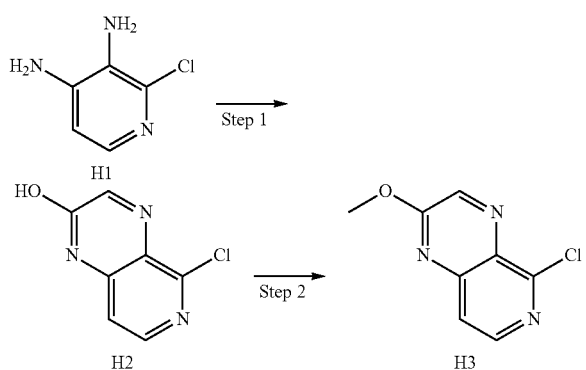

Step 1

To a stirred solution of 2-chloropyridine-3,4-diamine H1 (1.36 g, 9.45 mmol) in EtOH (95 ml) was added glyoxylic acid monohydrate (4.35 g, 47.3 mmol) at RT. The reaction was stirred at 70° C. for 15 h, then cooled to RT and concentrated. The residue was purified directly without workup by silica column chromatography (0-100% EtOAc in DCM) to give compound H2. MS for H2: m/e=182 (M+1).

Step 2

Intermediate H2 (1.24 g, 6.83 mmol) was dissolved in DCM (30.7 mL) and MeOH (3.41 mL). To this solution at 0° C. was added TMS-diazomethane (0.5 M in diethyl ether, 5.12 mL, 10.24 mmol) slowly. After being stirred at RT for 2 h, the reaction mixture was cooled to 0° C. and acetic acid (1.96 mL, 34.1 mmol) was added. After 30 min, the reaction was quenched with saturated aqueous sodium bicarbonate and extracted with DCM three times. The combined organic layers were dried over magnesium sulfate, filtered, and concentrated; the residue was purified by silica column chromatography (0-30% EtOAc in hexanes) to afford compound H3. MS for H3: m/e=196 (M+1).

Method I

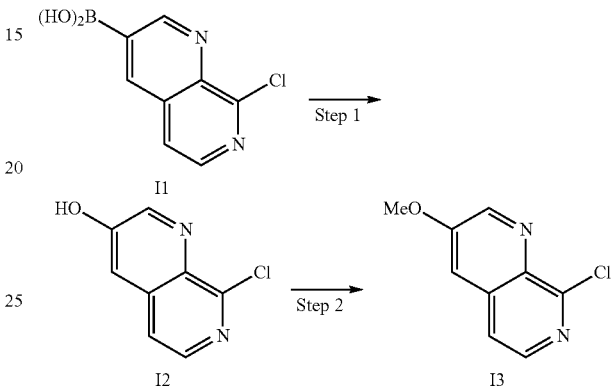

Step 1

To a solution of (8-chloro-1,7-naphthyridin-3-yl)boronic acid I1 (1.00 g, 4.80 mmol) in acetic acid (19.2 mL) was added hydrogen peroxide (2.10 mL, 24.0 mmol). The reaction mixture was stirred at RT for 4 h and poured over ice. To the solution was added slowly saturated sodium bicarbonate solution until the aqueous layer is slightly basic. The resulting mixture was extracted with EtOAc three times. The combined organic extracts were dried over magnesium sulfate, filtered, and concentrated. The residue was purified by silica column chromatography (0-10% MeOH in DCM) to give compound I2. MS for I2: m/e=181 (M+1).

Step 2

To a stirred solution of intermediate I2 (0.361 g, 2.00 mmol) and cesium carbonate (0.977 g, 3.00 mmol) in DMF (8.00 ml) was added methyl iodide (0.187 ml, 3.00 mmol). The reaction mixture was stirred at room temperature for 2 h, then diluted with water and extracted with DCM three times. The combined organic layers were dried over magnesium sulfate, filtered, and concentrated. The residue was purified by silica column chromatography (0-100% EtOAc in hexanes) to give compound I3. MS for I3: m/e=195 (M+1).

Method J

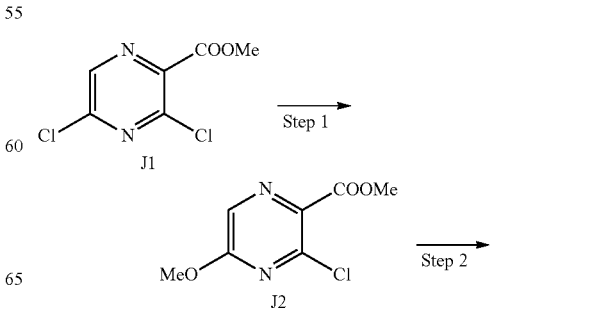

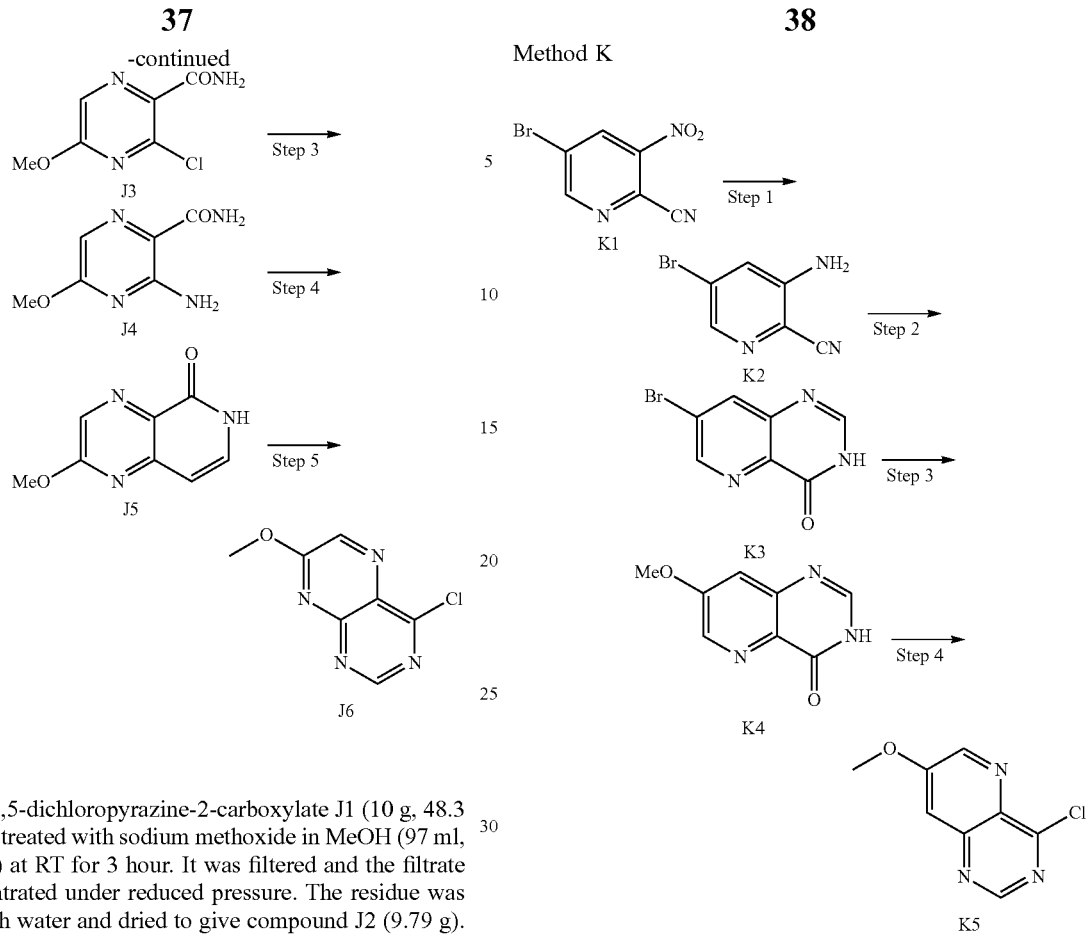

Method K

Step 1
Methyl 3,5-dichloropyrazine-2-carboxylate J1 (10 g, 48.3 mmol) was treated with sodium methoxide in MeOH (97 ml, 48.3 mmol) at RT for 3 hour. It was filtered and the filtrate was concentrated under reduced pressure. The residue was washed with water and dried to give compound J2 (9.79 g). LCMS for J2: m/e=203 (M+1).

Step 2
To a stirred solution of methyl 3-chloro-5-methoxypyrazine-2-carboxylate J2 (5 g, 24.68 mmol) in MeOH (30 ml) at room temperature was added ammonia (42.9 ml, 28% aq). The mixture was stirred at 60° C. for 3 hour; the precipitate was collected by filtration and washed with water to give compound J3 (4.4 g). LCMS for J3: m/e=188 (M+1).

Step 3
In a sealed tube were added 3-chloro-5-methoxypyrazine-2-carboxamide J3 (1.56 g, 8.32 mmol) and ammonia (100 ml, 0.5 M in dioxane). The reaction mixture was stirred at 105° C. overnight and cooled. It was filtered and washed by dioxane; the filtrate was concentrated under reduced pressure to give compound J4 (1.1 g). LCMS for J4: m/e=169 (M+1).

Step 4
To a stirred mixture of 3-amino-5-methoxypyrazine-2-carboxamide J4 (1.2 g, 7.14 mmol) and triethyl orthoformate (39.2 ml, 235 mmol) was added anhydride (39.7 ml, 421 mmol) at room temperature. The mixture was stirred at 150° C. for 1 h and cooled to RT, the mixture was concentrated under reduced pressure to give compound J5 (1.02 g). LCMS for J5: m/e=179 (M+1).

Step 5
A mixture of phosphorus oxychloride (13.8 ml, 149 mmol) and 7-methoxypteridin-4(3H)-one J5 (700 mg, 3.93 mmol) was stirred at 75° C. for 3 h. Then the excess phosphorus oxychloride was evaporated under reduced pressure. The residue was purified by column chromatography (40 g of $SiO_2$, 0-100% EtOAc/Hexane) to give compound J6 (580 mg). LCMS for J6: m/e=197 (M+1).

Step 1
To a cooled solution of compound K1 (5 g, 21.9 mmol) in concentrated HCl (30 mL) was added $SnCl_2.H_2O$ (24.7 g, 109.5 mmol) in several portions. After the addition was complete, the mixture was stirred at room temperature overnight. TLC (PE:EA=3:1) showed the reaction was complete. The mixture was basified with sodium carbonate (aq.) and extracted with ethyl acetate. The combined extracts were washed with brine, dried over sodium sulfate and filtered. The filtrate was concentrated; the residue was purified by column chromatography (PE:EA=20:1 to 5:1) to give compound K2 (1.9 g). MS for K2: m/e=198 and 200 (M+1).

Step 2
A mixture of compound K2 (1 g, 5.05 mmol) and sodium acetate (829 mg, 10.1 mmol) in formic acid (50 mL) was stirred at reflux overnight, and then concentrated. Sodium hydroxide (3M) was added to the residue; the mixture was stirred for 10 min and filtered. The solid was washed with water and resuspended in hydrochloride (3M), stirred for another 10 min. The solid was collected and dried to give compound K3 (0.8 g). MS for K3: m/e=226 and 228 (M+1).

Step 3
Sodium (0.3 g, 13.27 mmol) was added to MeOH (5 mL) and the solution was stirred at 18° C. for 20 min and concentrated. To the residue was added compound K3 (1 g, 4.42 mmol), DMF (10 mL) and CuI (0.421 g, 2.21 mmol). The mixture was stirred at 50° C. for 18 h and then concentrated to give crude compound K4. It was used in the next step without further purification. MS for K4: m/e=178 (M+1).

Step 4
To a solution of compound K4 (1.3 g, 3.67 mmol, crude) and DIEA (1.423 g, 11.01 mmol) in toluene (20 mL) was added POCl$_3$ (1.688 g, 11.01 mmol) carefully at room temperature. The mixture was stirred at 90° C. for 1 h, cooled and purified directly by column chromatography (SiO$_2$, PE:EtOAc=3:1 to 1:1) to give compound K5 (125 mg, 0.607 mmol). MS for K5: m/e=196 (M+1).

Method L

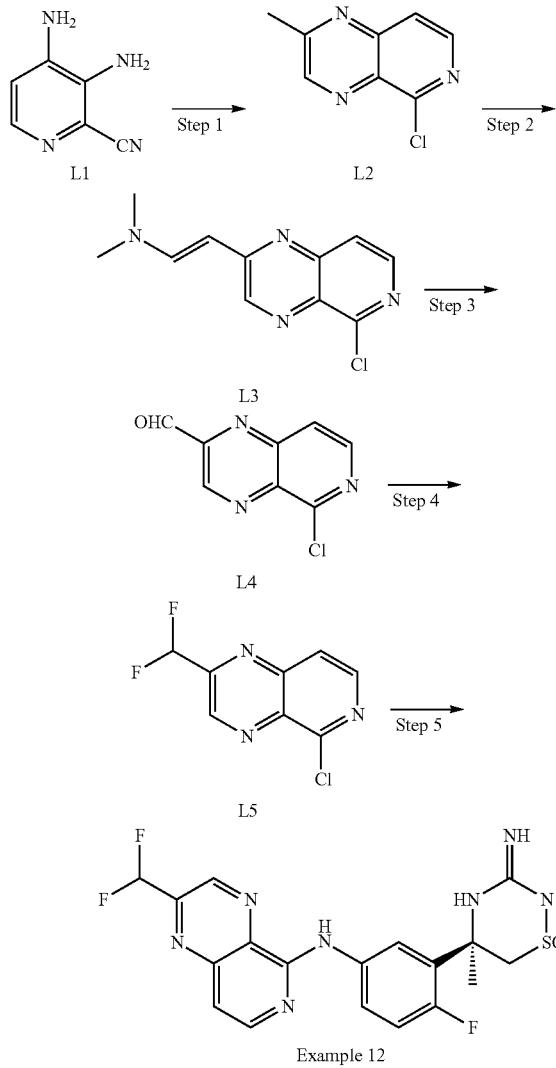

Example 12

Step 1

To a suspension of compound L1 (5 g, 34.8 mmol) in ethanol (70 mL) was added 2-oxopropanal (5.02 g, 69.7 mmol). The mixture was stirred at 20° C. until a clear solution was obtained. The final orange solution was heated at 90° C. for 48 h and concentrated. The residue was purified by chromatography on silica (PE:EtOAc=5:1~1:1) to afford L2. MS for L2: m/e=180 (M+1). $^1$H NMR for C-3 (400 MHz, CDCl$_3$): δ ppm 8.92 (s, 1H), 8.57 (d, J=5.9 Hz, 1H), 7.82 (d, J=5.5 Hz, 1H), 2.87 (s, 3H)

Step 2

To a solution of compound L2 (1 g, 5.57 mmol) in DMF (14 mL) was added DMF-DMA (2.236 mL, 16.70 mmol). The black mixture was then heated at 90° C. for 16 h and concentrated in vacuo. The residue was purified by chromatography on silica (PE:EtOAc=5:1~2:1) to afford L3. $^1$H NMR for L3 (400 MHz, DMSO-d$_6$): δ ppm 8.70 (br. s., 1H), 8.23 (d, J=5.5 Hz, 1H), 8.07 (d, J=12.5 Hz, 1H), 7.42 (d, J=5.9 Hz, 1H), 5.42 (d, J=12.5 Hz, 1H), 3.18 (br. s., 3H), 2.94 (br. s., 3H).

Step 3

To an ice-cooled solution of compound L3 (636 mg, 2.71 mmol) in THF (9 mL) and water (5 mL) was added sodium periodate (1159 mg, 5.42 mmol). The mixture was stirred at 20° C. for 5 h and partitioned between water and EtOAc. The aqueous layer was extracted with EtOAc. The combined organic extracts were dried over sodium sulfate, filtered and concentrated in vacuo. The residue was purified by chromatography on silica (PE:EtOAc=5:1~1:1) to afford L4. $^1$H NMR for L4 (400 MHz, CDCl$_3$): δ ppm 10.26 (s, 1H), 9.50 (s, 1H), 8.67 (d, J=5.5 Hz, 1H), 7.99 (d, J=5.5 Hz, 1H).

Step 4

To a solution of compound L4 (45 mg, 0.232 mmol) in DCM (1 mL) at −78° C. was added DAST (0.092 mL, 0.697 mmol) under nitrogen. The reaction mixture was stirred at 20° C. for 1 h and poured into ice-water. The aqueous layer was extracted with DCM; the combined organic extracts were dried over sodium sulfate, filtered and concentrated in vacuo to give compound L5. $^1$H NMR for L5 (400 MHz, CDCl3): δ ppm 9.36 (s, 1H), 8.70 (d, J=5.9 Hz, 1H), 7.97 (d, J=5.5 Hz, 1H), 7.09~6.70 (m, 1H).

Step 5

To a solution of (R,E)-tert-butyl (5-(5-amino-2-fluorophenyl)-2,5-dimethyl-1,1-dioxido-1,2,4-thiadiazinan-3-ylidene)carbamate A9 (89 mg, 0.231 mmol) and compound L5 (60 mg, 0.231 mmol) in BuOH (2 mL) was added a solution of HCl in dioxane (0.115 mL, 0.46 mmol). The reaction vessel was sealed and stirred at 100° C. for 0.5 h. Then it was diluted with water, neutralized with NaHCO$_3$, and extracted with EtOAc. The combined extracts were dried over Na$_2$SO$_4$ and concentrated. The residue was purified by prep-HPLC (ACN/water with 0.1% TFA modifier) to afford example 12 as the TFA salt. MS for example 12: m/e=466 (M+1)

Method M

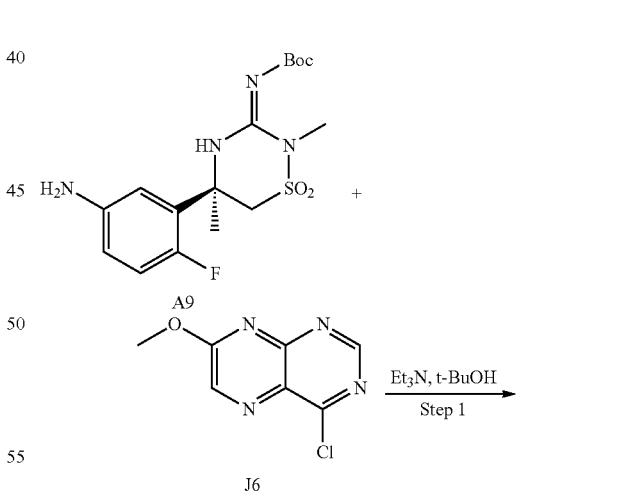

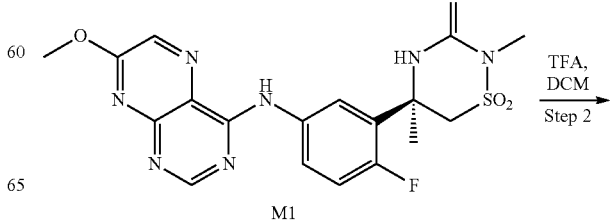

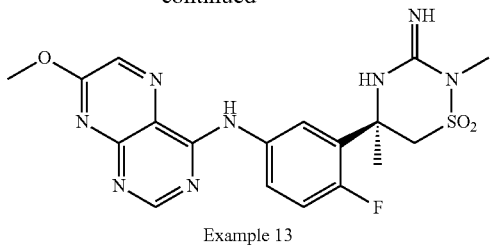

Example 13

Step 1

A mixture of (R)-tert-butyl (5-(5-amino-2-fluorophenyl)-2,5-dimethyl-1,1-dioxido-1,2,4-thiadiazinan-3-ylidene)carbamate A9 (79 mg, 0.203 mmol) and 4-chloro-7-methoxypteridine J6 (40 mg, 0.203 mmol) in t-BuOH (4 mL) was added triethylamine (61.8 mg, 0.610 mmol) under $N_2$. The mixture was stirred at 75° C. for 1 h and cooled to rt. Then it was diluted with water (5 mL) and extracted with EtOAc (3×6 mL). The organic phase was washed with brine (15 mL), dried over $Na_2SO_4$ and concentrated to afford M1. MS for M1: m/e=547 (M+1).

Step 2

To a solution of (R)-tert-butyl (5-(5-fluoro-2-((7-methoxypteridin-4-yl)amino) pyridin-4-yl)-2,5-dimethyl-1,1-dioxido-1,2,4-thiadiazinan-3-ylidene)carbamate M1 (100 mg, 0.183 mmol) in DCM (6 mL) was added 2,2,2-trifluoroacetic acid (2 mL, 0.183 mmol) at 18° C. The mixture was stirred at 18° C. for 1 h and neutralized with $NaHCO_3$ (5 mL, 5 M). The aqueous phase was extracted with EtOAc (4×5 mL); the combined organic extracts were washed with brine (10 mL), dried over $Na_2SO_4$ and concentrated. The residue was purified by prep-HPLC (ACN/water with 0.1% TFA modifier) to afford example 13 as the TFA salt. MS for example 13: m/e=447 (M+1).

Method N

A mixture of (R)-tert-butyl (5-(5-amino-2-fluorophenyl)-2,5-dimethyl-1,1-dioxido-1,2,4-thiadiazinan-3-ylidene)carbamate A9 (49.4 mg, 0.128 mmol), 4-chloro-7-methoxypyrido[3,2-d]pyrimidine K5 (25 mg, 0.128 mmol) and HCl in dioxane (4 M, 72 uL) was stirred at 100° C. for 1 h until the reaction was complete. The mixture was neutralized with saturated $NaHCO_3$ (3 mL), extracted with EtOAc (5 mL×4). The combined organic layers were washed with brine (5 mL), dried over sodium sulfate, and filtered. The filtrate was concentrated in vacuo, and the residue was purified by prep-HPLC (ACN/water with 0.05% $NH_3H_2O$ modifier) to afford example 14. MS for example 14: m/e=446 (M+1).

Method O

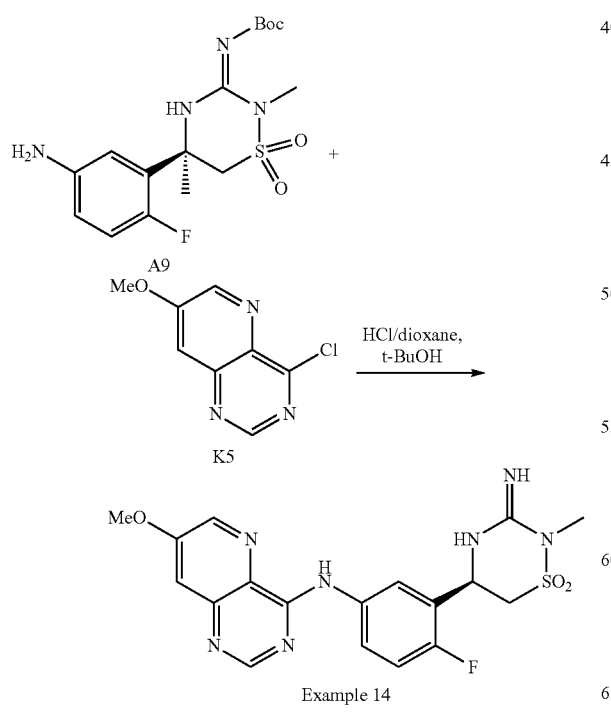

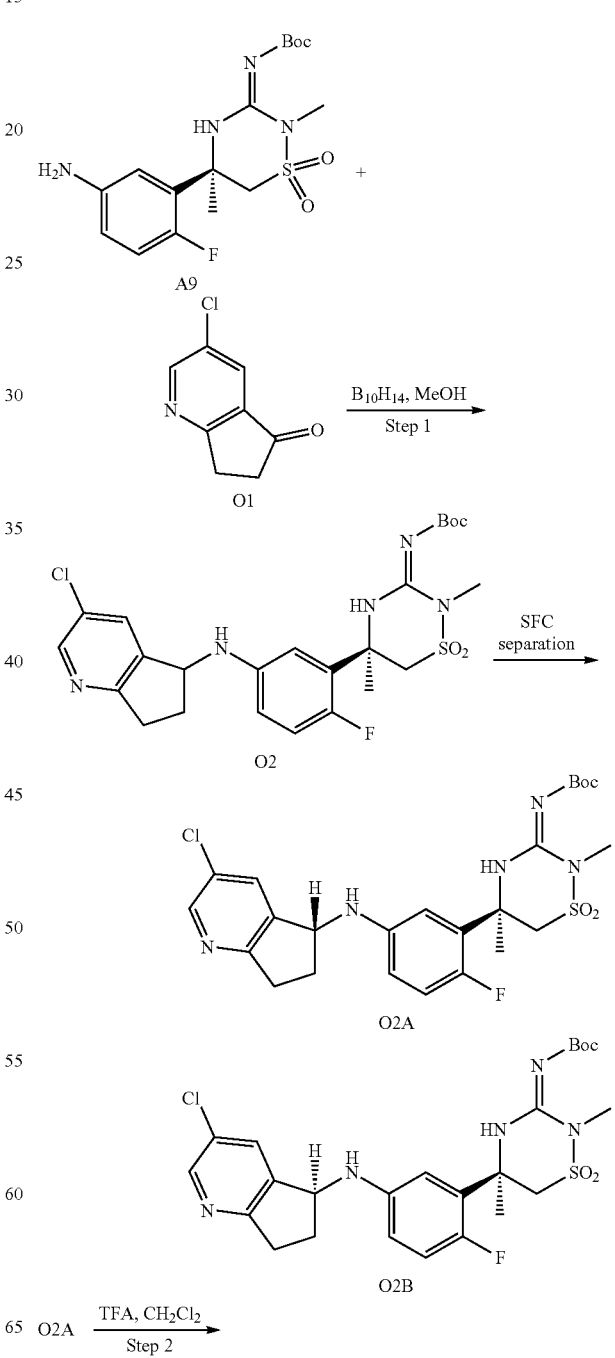

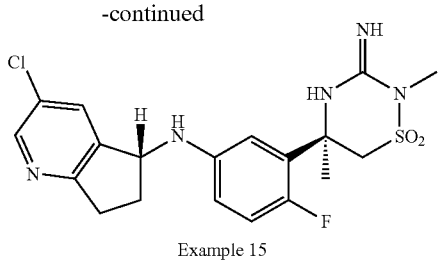

Example 15

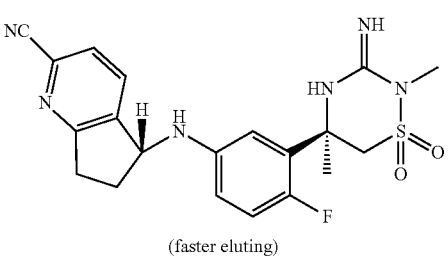

Example 18
(faster eluting)

Step 1

A mixture of (R)-tert-butyl (5-(5-amino-2-fluorophenyl)-2,5-dimethyl-1,1-dioxido-1,2,4-thiadiazinan-3-ylidene)carbamate A9 (150 mg, 0.388 mmol) and 3-chloro-6,7-dihydro-5H-cyclopenta[b]pyridin-5-one O1 (65.1 mg, 0.388 mmol) in methanol (1.9 mL) at RT was treated with decaborane (14.2 mg, 0.166 mmol) and the mixture was stirred for 12 h. The mixture was partitioned between saturated aqueous sodium bicarbonate and EtOAc and the layers separated. The aqueous layer was extracted with EtOAc (2×) and the combined organic layers were washed with brine (5 mL), dried over sodium sulfate, and filtered. The filtrate was concentrated in vacuo, and the residue was purified by chiral SFC chromatography (30 mm×250 mm IC column, 30% MeOH/CO₂, 70 mL/min., 100 bar, 35 C) to afford O2A (faster eluting) and O2B (slower eluting). MS for O2A: m/e=538 (M+1); O2B: m/e=538 (M+1).

Step 2

To a solution of O2A (70.0 mg, 0.130 mmol) in dichloromethane (1 mL) at RT was added TFA (0.20 mL, 2.60 mmol) and the mixture stirred 1.5 h. The mixture was concentrated in vacuo and dried under high vacuum. The resulting residue was purified by chiral chromatography (30 mm×250 mm OD column, 40% MeOH/CO₂, 70 mL/min., 100 bar, 35 C) to provide example 15. MS for example 15: m/e=438 (M+1).

Using similar chemistry to that described in Method O, the following examples were prepared:

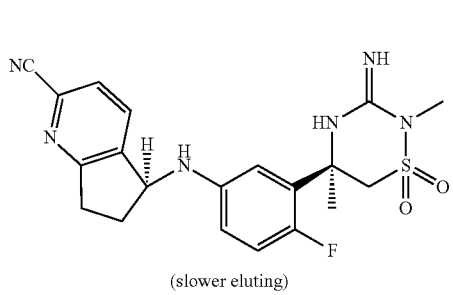

Example 19
(slower eluting)

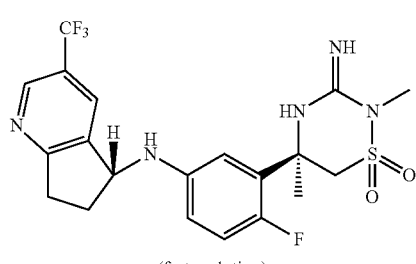

Example 16
(faster eluting)

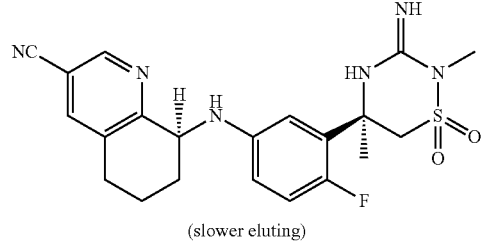

Example 20
(slower eluting)

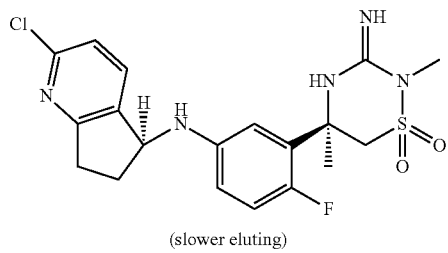

Example 17
(slower eluting)

Non-limiting examples of compounds of the invention are shown in Table 1. As noted above, while only one tautomeric form of each compound is shown in the table, it shall be understood that both tautomeric forms of each compound are contemplated as being within the scope of the non-limiting examples.

TABLE 1

| Ex | Structure / IUPAC Name | LCMS m/z | BACE1 $K_i$ (nM) | BACE2 $K_i$ (nM) |
|---|---|---|---|---|
| 1 | 3-chloro-N-{4-fluoro-3-[(5R)-3-imino-2,5-dimethyl-1,1-dioxido-1,2,4-thiadiazinan-5-yl]phenyl}-1,7-naphthyridin-8-amine | 449 | 1.2 | 0.22 |
| 2 | 3-bromo-N-{4-fluoro-3-[(5R)-3-imino-2,5-dimethyl-1,1-dioxido-1,2,4-thiadiazinan-5-yl]phenyl}-1,7-naphthyridin-8-amine | 493 | 1.5 | 0.38 |
| 3 | 7-bromo-N-{4-fluoro-3-[(5R)-3-imino-2,5-dimethyl-1,1-dioxido-1,2,4-thiadiazinan-5-yl]phenyl}pyrido[3,2-d]pyrimidin-4-amine | 494 | 2.8 | 0.81 |
| 4 | N-{4-fluoro-3-[(5R)-3-imino-2,5-dimethyl-1,1-dioxido-1,2,4-thiadiazinan-5-yl]phenyl}-3-methoxy-1,7-naphthyridin-8-amine | 445 | 11.7 | 5.8 |
| 5 | N-{5-fluoro-4-[(5R)-3-imino-2,5-dimethyl-1,1-dioxido-1,2,4-thiadiazinan-5-yl]pyridin-2-yl}-3-methoxy-1,7-naphthyridin-8-amine | 446 | 16.2 | 4.5 |

TABLE 1-continued

| Ex | Structure / IUPAC Name | LCMS m/z | BACE1 $K_i$ (nM) | BACE2 $K_i$ (nM) |
|---|---|---|---|---|
| 6 | 8-({4-fluoro-3-[(5R)-3-imino-2,5-dimethyl-1,1-dioxido-1,2,4-thiadiazinan-5-yl]phenyl}amino)-1,7-naphthyridine-3-carbonitrile | 440 | 1.31 | 0.46 |
| 7 | 4-({4-fluoro-3-[(5R)-3-imino-2,5-dimethyl-1,1-dioxido-1,2,4-thiadiazinan-5-yl]phenyl}amino)pyrido[3,2-d]pyrimidine-7-carbonitrile | 441 | 3.2 | 3.0 |
| 8 | 3-fluoro-N-{4-fluoro-3-[(5R)-3-imino-2,5-dimethyl-1,1-dioxido-1,2,4-thiadiazinan-5-yl]phenyl}-1,7-naphthyridin-8-amine | 433 | 2.1 | 0.24 |
| 9 | N-{4-fluoro-3-[(5R)-3-imino-2,5-dimethyl-1,1-dioxido-1,2,4-thiadiazinan-5-yl]phenyl}-2-methoxypyrido[3,4-b]pyrazin-5-amine | 446 | 2.6 | 3.5 |
| 10 | N-{5-fluoro-4-[(5R)-3-imino-2,5-dimethyl-1,1-dioxido-1,2,4-thiadiazinan-5-yl]pyridin-2-yl}-2-methoxypyrido[3,4-b]pyrazin-5-amine | 447 | 19.3 | 6.9 |

TABLE 1-continued

| Ex | Structure / IUPAC Name | LCMS m/z | BACE1 K$_i$ (nM) | BACE2 K$_i$ (nM) |
|---|---|---|---|---|
| 11 | 8-({2,4-difluoro-3-[(5R)-3-imino-2,5-dimethyl-1,1-dioxido-1,2,4-thiadiazinan-5-yl]phenyl}amino)-1,7-naphthyridine-3-carbonitrile | 458 | 2.1 | 1.1 |
| 12 | 2-(difluoromethyl)-N-{4-fluoro-3-[(5R)-3-imino-2,5-dimethyl-1,1-dioxido-1,2,4-thiadiazinan-5-yl]phenyl}pyrido[3,4-b]pyrazin-5-amine | 466 | 5.2 | 1.8 |
| 13 | N-{4-fluoro-3-[(5R)-3-imino-2,5-dimethyl-1,1-dioxido-1,2,4-thiadiazinan-5-yl]phenyl}-7-methoxypteridin-4-amine | 447 | 10.6 | 15.4 |
| 14 | N-{4-fluoro-3-[(5R)-3-imino-2,5-dimethyl-1,1-dioxido-1,2,4-thiadiazinan-5-yl]phenyl}-7-methoxypyrido[3,2-d]pyrimidin-4-amine | 446 | 4.3 | 4.4 |
| 15 | (R)-5-(5-(((R)-3-chloro-6,7-dihydro-5H-cyclopenta[b]pyridin-5-yl)amino)-2-fluorophenyl)-3-imino-2,5-dimethyl-1,2,4-thiadiazinane 1,1-dioxide | 438 | 41.2 | 124 |

TABLE 1-continued

| Ex | Structure / IUPAC Name | LCMS m/z | BACE1 K$_i$ (nM) | BACE2 K$_i$ (nM) |
|---|---|---|---|---|
| 16 | (R)-5-(2-fluoro-5-(((R)-3-(trifluoromethyl)-6,7-dihydro-5H-cyclopenta[b]pyridin-5-yl)amino)phenyl)-3-imino-2,5-dimethyl-1,2,4-thiadiazinane 1,1-dioxide | 472 | 57.3 | 242 |
| 17 | (R)-5-(5-(((S)-5-chloro-2,3-dihydro-1H-inden-1-yl)amino)-2-fluorophenyl)-3-imino-2,5-dimethyl-1,2,4-thiadiazinane 1,1-dioxide | 437 | 10.2 | 16.6 |
| 18 | (S)-7-((4-fluoro-3-((R)-3-imino-2,5-dimethyl-1,1-dioxido-1,2,4-thiadiazinan-5-yl)phenyl)amino)-6,7-dihydro-5H-cyclopenta[b]pyridine-3-carbonitrile | 429 | 3.1 | 22.3 |
| 19 | (R)-7-((4-fluoro-3-((R)-3-imino-2,5-dimethyl-1,1-dioxido-1,2,4-thiadiazinan-5-yl)phenyl)amino)-6,7-dihydro-5H-cyclopenta[b]pyridine-3-carbonitrile | 429 | 81 | 42.6 |
| 20 | (R)-5-(5-(((S)-3-bromo-5,6,7,8-tetrahydroquinolin-8-yl)amino)-2-fluorophenyl)-3-imino-2,5-dimethyl-1,2,4-thiadiazinane 1,1-dioxide | 496 | 127.5 | 43.1 |

Biological Assays

Protocols that may be used to determine the recited biological properties for the compounds of the invention are described below.

Assay 1: BACE-1 Ki Assay (BACE-1 HTRF FRET Assay)

The compounds of the invention were assessed for their ability to inhibit BACE-1 using the following assay. The resulting values are reported in the table above.

The following reagents were used in this assay. Na$^+$-Acetate pH 5.0; 1% Brij-35; Glycerol; Dimethyl Sulfoxide (DMSO); Recombinant human soluble BACE-1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine $IC_{50}$ values for inhibitors of the soluble human BACE-1 catalytic domain. This assay monitors the increase of 620 nm fluorescence that resulted from BACE-1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE-1 enzyme. Inhibition of BACE-1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE-1 catalytic domain (3 nM in 10 µl) for 30 minutes at 30° C. in reaction buffer containing 20 mM Na-Acetate pH 5.0, 10% glycerol, 0.1% Brij-35 and 7.5% DSMO. Reactions are initiated by addition of 10 µl of 600 nM QSY7-APP$^{swe}$-Eu substrate (200 nM final) to give a final reaction volume of 30 µl in a 384 well Nunc HTRF plate. The reactions are incubated at 30° C. for 1.5 hours. The 620 nm fluorescence is then read on a Rubystar HTRF plate reader (BMG Labtechnologies) using a 50 milisecond delay followed by a 400 millisecond acquisition time window. Inhibitor $IC_{50}$ values are derived from non-linear regression analysis of concentration response curves. $K_i$ values are then calculated from $IC_{50}$ values using the Cheng-Prusoff equation using a previously determined µm value of 8 µM for the QSY7-APP$^{swe}$-Eu substrate at BACE-1. The example compounds of the invention were measured in this assay. Their measured Ki values are reported in the table above.

Assay 2: BACE-2 Assay

The compounds of the invention were assessed for their ability to inhibit BACE-1 using the following assay. The resulting values are reported in the table above.

Inhibitor $IC_{50s}$ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1× BACE assay buffer (20 mM sodium acetate pH 5.0, 10% glycerol, 0.1% Brij-35) supplemented with 7.5% DMSO are pre-incubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 µM for 4 µM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 µs delay on a RUBYstar HTRF plate reader (BMG Labtechnologies). Raw RFU data is normalized to maximum (1.0 nM BACE/DMSO) and minimum (no enzyme/DMSO) RFU values. $IC_{50}$ values are determined by nonlinear regression analysis (sigmoidal dose response, variable slope) of percent inhibition data with minimum and maximum values set to 0 and 100 percent respectively. Similar $IC_{50s}$ are obtained when using raw RFU data. The $K_i$ values are calculated from the $IC_{50}$ using the Cheng-Prusoff equation.

Assay 3: Aβ Reduction In Vivo

Certain compounds of the invention were determined to exhibit unexpectedly improved reduction of amyloid beta peptide (Aβ) levels in vivo. The in vivo efficacy and/or potency of BACE inhibitors (test compounds) can be evaluated using a variety of animal models, including mouse, rat, dog, and monkey, and these animals can be wild type, transgenic, or gene knockout animals.

Generally, animals are administered (by oral gavage, intravenous injection, or by other suitable route) a test compound in doses ranging from, for example, 0.1 mg/kg (mg of compound per kg of animal body weight) to 100 mg/kg formulated in vehicles, such as cyclodextrin, phosphate buffer, hydroxypropyl methylcellulose or other suitable vehicles. One to twenty-four hours following the administration of compound, animals are sacrificed, and tissues (for example, brain, cerebrospinal fluid (CSF), and/or plasma) are collected for analysis of Aβ levels and/or test compound concentrations (Dovey et al., 2001, *Journal of Neurochemistry*, 76, 173-181). Tissue samples are processed appropriately and then analyzed for the presence of Aβ by specific sandwich ELISA assays based on electrochemiluminescence (ECL) technology. Changes in Aβ levels are then reported as percent change relative to levels in comparable animals treated only with vehicle but otherwise processed as described above for test compound-treated animals.

For example, in the following assay for which data are reported below, male CD IGS rats (body weight approximately 120 g, Charles River Laboratories, Kingston, N.Y.) were used to asses lowering of CSF levels of $Aβ_{1-40}$ ($Aβ_{40}$) in the presence of compounds of the invention. At time 0, animals were administered by oral gavage a test compound at a dose of 10 mg/kg in 20% hydroxypropyl-β-cyclodextrin (dosing volume 5 mL/kg). A separate group of animals received 20% hydroxypropyl-β-cyclodextrin alone to serve as the vehicle control group. Three hours after administration, the rats were euthanized with excess $CO_2$. Immediately following euthanasia, CSF was collected from the cisterna magna and quickly frozen on dry ice. Samples were stored at −80° C. until quantification of $Aβ_{40}$ levels.

The measurement of endogenous rat $Aβ_{40}$ in CSF relied on the 585 antibody (Ab585, BioSource, NONO585), which specifically recognizes the N-terminal sequence of rodent $Aβ_{40}$, and on the monoclonal antibody, G2-10, which specifically recognizes the free C-terminus of $Aβ_{40}$. Ab585 was labeled with biotin (b-Ab585) by first dialyzing the antibody sample extensively versus PBS (pH 7.8) to remove impurities, followed by dilution to between 1 and 2 mg/mL protein concentration. EZ-Link Sulfo-NHS-LC-Biotin (Pierce) was dissolved in PBS (pH 7.8) at a concentration of 1 mg/mL immediately prior to use. Ab585 was labeled with EZ-Link Sulfo-NHS-LC-biotin using a 10:1 biotin:antibody ratio by incubation at room temperature for 1 hour. The labeling reaction was quenched by addition of 1.0 M glycine to a final concentration of 0.1 M followed by 10 minute incubation at room temperature. Glycine was removed by extensive dialysis versus PBS.

For rat CSF $A\beta_{40}$ determinations, a calibration curve of various concentrations of synthetic rodent $A\beta_{40}$ was assayed in parallel with rat CSF samples in duplicate using an avidin-coated 96-well MSD plate (Mesoscale Diagnostics). Either 50 μL of rodent $A\beta_{40}$ standards diluted in PBS (pH 7.4) supplemented with 1% BSA and 1% Tween-20 (standard diluent buffer) or 40 μL of standard diluent buffer plus 10 μL rat CSF were added to each 96 well avidin-coated plate. To each well was added 50 μL of 0.1 M HEPES (pH 7.5), 2% BSA, 2% Tween-20, 0.3 M NaCl (2× $A\beta_{40}$ buffer) supplemented with the b-Ab585 capture and ruthenylated-G2-10 detection antibodies diluted to 1 μg/mL and 0.5 μg/mL, respectively. Plates were shaken for 1 min on a microplate shaker, covered to protect from light and incubated overnight (~16 h) at 4° C. For detection, plates were first washed twice with 100 μL of 1×CSF $A\beta_{40}$ buffer followed by addition of 160 μL of 1×MSD read buffer-T (Mesoscale Diagnostics) diluted in 1×CSF $A\beta_{40}$ buffer. Plates were read on a MSD Sector Imager 2400 model (Mesoscale Diagnosotics). Data were analyzed using Graph-Pad Prism and were either plotted as raw counts or absolute $A\beta_{40}$ calculated from the rodent $A\beta_{40}$ standard curve. Percent change values for each test compound were calculated by normalization of the average absolute CSF $A\beta_{40}$ levels in each test compound-treated cohort to the average absolute CSF $A\beta_{40}$ levels in the vehicle cohort (Δ% CSF $A\beta_{40}$@10 mpk). Comparative results are shown in the table below.

As noted above, certain example compounds of the invention exhibit an unexpected and beneficial BACE-1 potency in the above described binding assay compared to compounds of WO2011044181 ("WO'181"). The following are examples of such compounds of the invention, which were measured in the above described assays: Examples 1-14, 17, and 18. Moreover, certain of these compounds of the invention exhibit an unexpected and beneficial combination of BACE-1 potency in a binding assay and ability to lower $A\beta_{40}$ levels in vivo when compared to those of WO2011044181 ("WO'181"). The measured values are listed in Table 2 below. Corresponding values for comparator compounds of WO'181 are shown in Table 3 below. ("-" means not tested.)

TABLE 2

| Example | BACE1 $K_i$ (nM) | Rat CSF Aβ40 |
|---|---|---|
| 4 | 12 | −45% |
| 6 | 1.3 | −50% |
| 7 | 3.2 | −21% |
| 8 | 2.1 | −21% |
| 9 | 2.6 | −68% |
| 11 | 2.1 | −50% |
| 12 | 5.2 | −44% |
| 14 | 4.3 | −55% |

TABLE 3

Comparitor compounds

| Example No. in WO'181 | Structure | BACE-1 Ki Nm | Rat CSF Aβ40 |
|---|---|---|---|
| 103 (Scheme 18) | 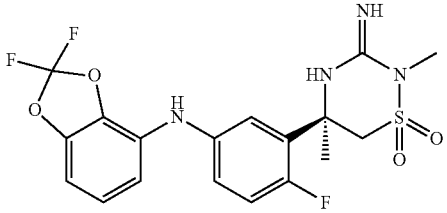 | 42 | — |
| 103a (Table IXa) | 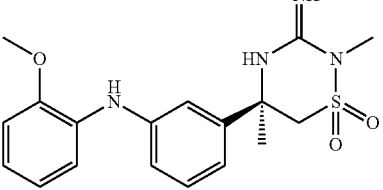 | 69 | — |
| 103b (Table IXa) | 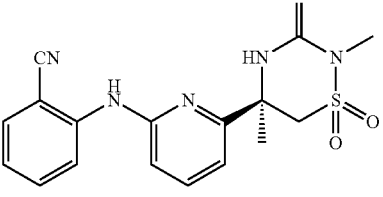 | 514 | — |

TABLE 3-continued

| | Comparitor compounds | | |
|---|---|---|---|
| Example No. in WO'181 | Structure | BACE-1 Ki Nm | Rat CSF Aβ40 |
| 162 (Scheme 40) | | 3756 | — |
| 163 (Table XXI) | | 4695 | — |
| 164 (Table XXI) | | 508 | — |
| 165 (Table XXI) | | 48 | −11% |
| 165 (as listed on page 224) | | 2592 | — |
| 166 (Table XXI) | | 41 | — |

TABLE 3-continued

Comparitor compounds

| Example No. in WO'181 | Structure | BACE-1 Ki Nm | Rat CSF Aβ40 |
|---|---|---|---|
| 167 (Table XXI) | 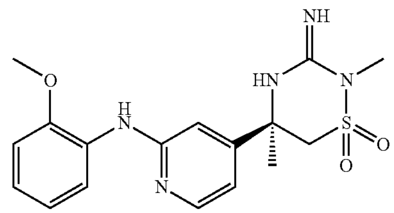 | 344 | — |

While the present invention has been described in view of the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound, or a pharmaceutically acceptable salt thereof, said compound having the structural Formula (I):

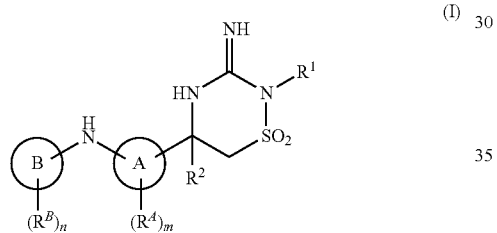

or a tautomer thereof having the structural Formula (I'):

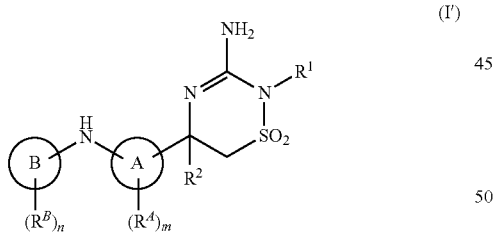

or pharmaceutically acceptable salt thereof, wherein:
$R^1$ is selected from the group consisting of H, lower alkyl, lower cycloalkyl, and -(lower alkyl)-(lower cycloalkyl),
wherein said lower alkyl, lower cycloalkyl, and -(lower alkyl)-(lower cycloalkyl) are optionally substituted with one or more fluorine, and
wherein 1 to 2 non-adjacent, non-terminal carbon atoms in said alkyl are optionally independently replaced with —O—, —NH—, —N-(lower alkyl)-, —S—, —S(O)—, or —S(O)$_2$—;
$R^2$ is selected from the group consisting of H, lower alkyl, lower cycloalkyl, and -(lower alkyl)-(lower cycloalkyl),
wherein said lower alkyl, lower cycloalkyl, and -(lower alkyl)-(lower cycloalkyl) are optionally substituted with one or more fluorine, and
wherein 1 to 2 non-adjacent, non-terminal carbon atoms in said alkyl are optionally independently replaced with —O—, —NH—, —N-(lower alkyl)-, —S—, —S(O)—, or —S(O)$_2$—;
ring A is selected from the group consisting of phenyl, pyridinyl, pyridazinyl, pyrimidinyl, and pyrazinyl;
m is 0, 1, 2, or 3;
each $R^A$ (when present) is independently selected from the group consisting of halogen, —CN, —OCH$_3$, —O-cyclopropyl, methyl, cyclopropyl, —CH$_2$OCH$_3$, —CF$_3$, —CHF$_2$, —CH$_2$F, —OCF$_3$, —OCHF$_2$, —OCH$_2$F, and —OCH$_2$CH$_2$F;
ring B is selected from the group consisting of benzimidazolyl, benzoisothiazolyl, benzoisoxazolyl, benzothiazolyl, benzoxazolyl, dihydrocyclopentapyridinyl, dihydroindenyl, imidazopyrazinyl, imidazopyridinyl, imidazopyrimidinyl, imidazothiazolyl, indenyl, indolyl, isoquinolinyl, naphthyridinyl, phthalazinyl, pteridinyl, pyrazinopyridazinyl, pyrazolopyridinyl, pyrazolopyrimidinyl, pyridopyrazinyl, pyridopyridazinyl, pyridopyrimidinyl, pyrrolopyridinyl, pyrrolopyrimidinyl, quinazolinyl, quinolinyl, quinoxalinyl, tetrahydroisoquinolinyl, tetrahydroquinolinyl, and thienylpyridinyl;
n is 0, 1, 2, or 3; and
each $R^B$ (when present) is independently selected from the group consisting of halogen, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —CH$_2$F, —OCF$_3$, —OCHF$_2$, —OCH$_2$F, and —OCH$_2$CH$_2$F.

2. A compound of claim 1, or a tautomer thereof, or a pharmaceutically acceptable salt of said compound or said tautomer, wherein:
$R^1$ is methyl; and
$R^2$ is methyl.

3. A compound of claim 2, or a tautomer thereof, or a pharmaceutically acceptable salt of said compound or said tautomer, wherein:
ring A is selected from the group consisting of phenyl, pyridinyl, and pyrimidinyl;
m is 0, 1 or 2; and
each $R^A$ (when present) is independently selected from the group consisting of fluoro, chloro, —CN, —OCH$_3$, —CF$_3$, —CHF$_2$, —CH$_2$F, —OCF$_3$, —OCHF$_2$, and —OCH$_2$F.

4. A compound of claim 3, or a tautomer thereof, or a pharmaceutically acceptable salt of said compound or said tautomer, wherein:

ring B is selected from the group consisting of dihydrocyclopentapyridinyl, dihydroindenyl, naphthyridinyl, pteridinyl, pyridopyrazinyl, pyridopyrimidinyl, and tetrahydroquinolinyl;

n is 0, 1, 2, or 3; and each $R^B$ (when present) is independently selected from the group consisting of fluoro, chloro, bromo, —CN, —OH, —CH$_3$, —CHF$_2$, —CH$_2$F, —OCH$_3$, —OCH$_2$—C≡C—H, and —OCH$_2$—C≡C—CH$_3$.

5. A compound of claim 3, or a tautomer thereof, or a pharmaceutically acceptable salt of said compound or said tautomer, wherein:

ring B, $R^B$, and n form a moiety selected from the group consisting of:

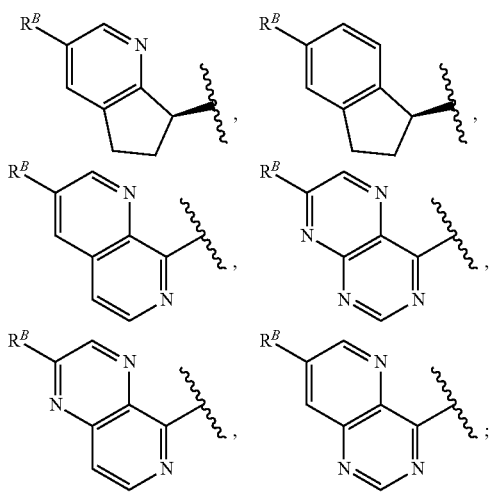

wherein $R^B$ is selected from the group consisting of fluoro, chloro, bromo, —CN, —OCH$_3$, —CHF$_2$, and —CF$_3$.

6. A compound of claim 3, or a tautomer thereof, or a pharmaceutically acceptable salt of said compound or said tautomer, wherein:

ring B, $R^B$, and n form a moiety selected from the group consisting of:

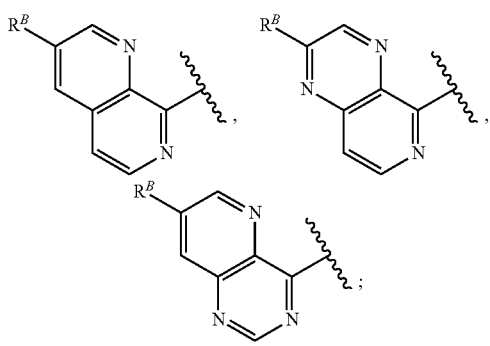

wherein $R^B$ is selected from the group consisting of fluoro, —CN, —OCH$_3$, and —CHF$_2$.

7. A compound of claim 1, or a tautomer thereof, or a pharmaceutically acceptable salt of said compound or said tautomer, said compound selected from the group consisting of:

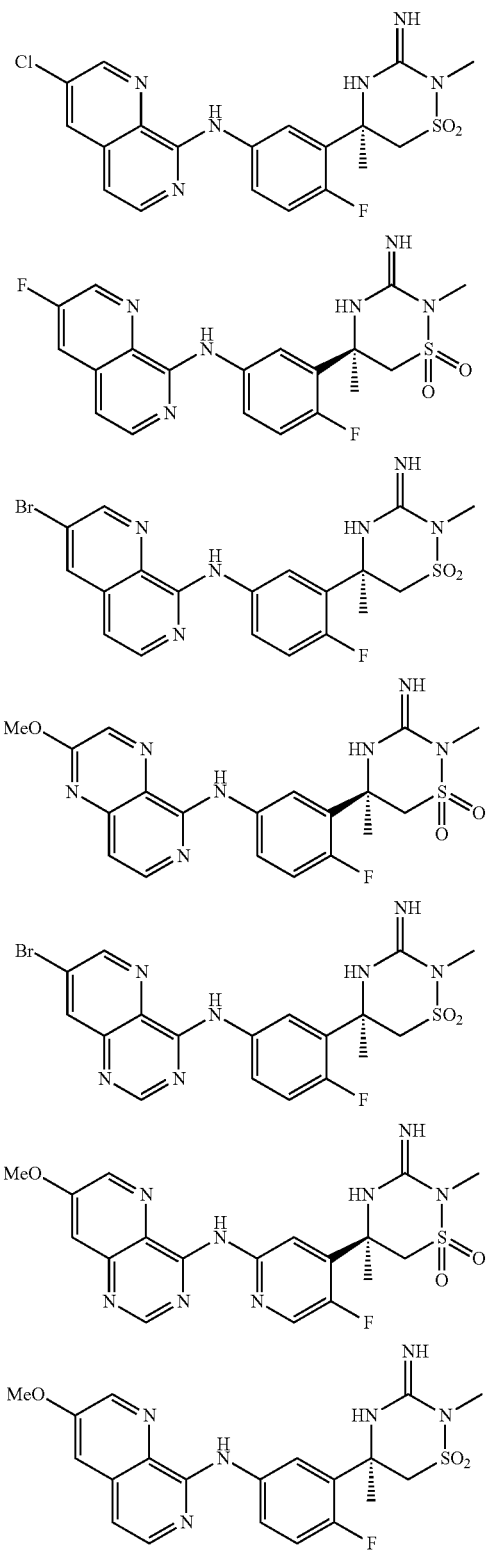

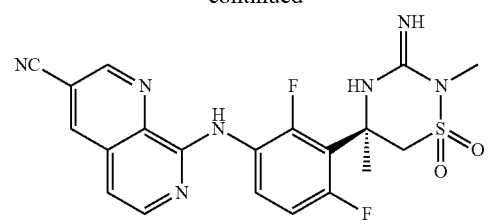

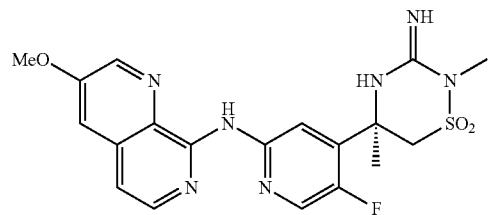 [SMILES: COc1cnc2c(Nc3cc([C@]4(C)CS(=O)(=O)N(C)C(=N)N4)c(F)cn3)nccc2c1]

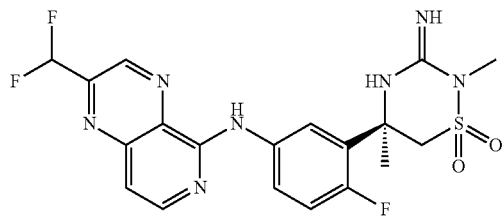

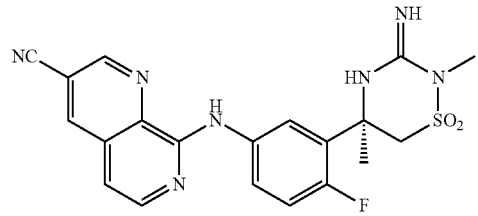 [SMILES: CN1C(=N)N[C@](C)(c2cc(Nc3nccc4cc(C#N)cnc34)ccc2F)CS1(=O)=O]

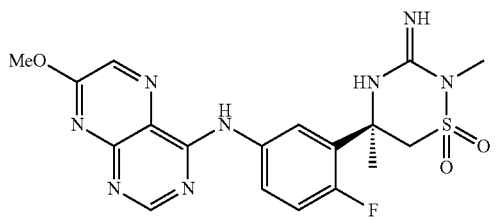

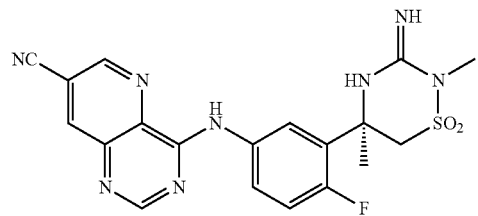 [SMILES: CN1C(=N)N[C@](C)(c2cc(Nc3ncnc4cc(C#N)cnc34)ccc2F)CS1(=O)=O]

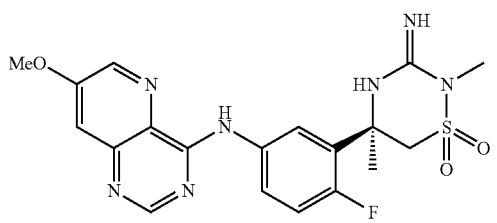

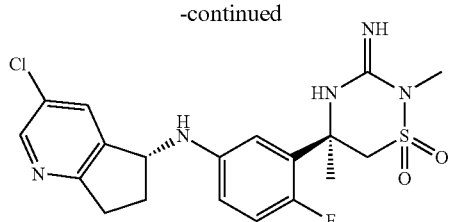

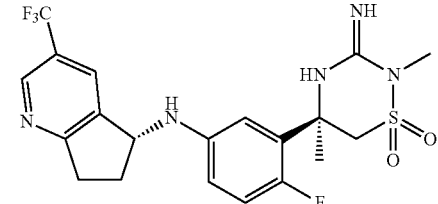

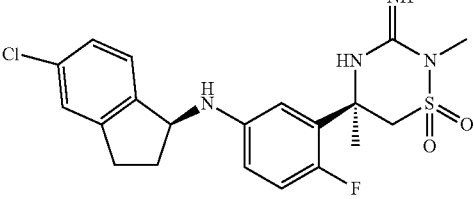

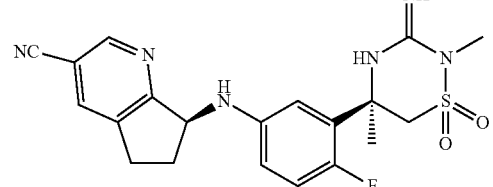

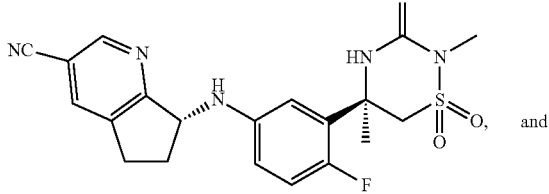, and

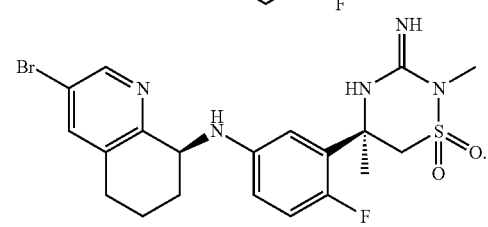.

8. A pharmaceutical composition comprising a compound according to claim, or a tautomer thereof, or a pharmaceutically acceptable salt of said compound or said tautomer, and a pharmaceutically acceptable carrier or diluent.

9. A method of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound according to claim, or a tautomer thereof, or a pharmaceutically acceptable salt of said compound or said tautomer, to a patient in need thereof in an amount effective to treat said disease or pathology.

10. The method of claim 9, wherein disease or pathology is Alzheimer's disease.

* * * * *